(12) United States Patent
Kugler et al.

(10) Patent No.: US 6,280,466 B1
(45) Date of Patent: Aug. 28, 2001

(54) ENDOVASCULAR GRAFT SYSTEM

(75) Inventors: Chad J. Kugler, Andover; John R. Drontle, Monticello; Matthew J. Olson, Maple Grove; Thomas K. Heiland, Brooklyn Park; Peter T. Keith, St. Paul, all of MN (US)

(73) Assignee: TERAMed Inc., Maple Grove, MN (US)

( * ) Notice: Subject to any disclaimer, the term of this patent is extended or adjusted under 35 U.S.C. 154(b) by 0 days.

(21) Appl. No.: 09/454,038

(22) Filed: Dec. 3, 1999

(51) Int. Cl.$^7$ ............................................. A61M 29/00
(52) U.S. Cl. ............................... 623/1.12; 623/1.15
(58) Field of Search ........................ 623/1.11, 1.35, 623/1.12, 1.15; 606/108, 194

(56) References Cited

U.S. PATENT DOCUMENTS

| | | |
|---|---|---|
| 4,562,596 | 1/1986 | Kornberg . |
| 4,577,631 | 3/1986 | Kreamer . |
| 4,617,932 | 10/1986 | Kornberg . |
| 4,787,899 | 11/1988 | Lazarus . |
| 4,994,071 | 2/1991 | MacGregor . |
| 5,122,154 | 6/1992 | Rhodes . |
| 5,123,917 | 6/1992 | Lee . |
| 5,290,295 | 3/1994 | Querals et al. ............... 606/108 |
| 5,316,023 | 5/1994 | Palmaz et al. ............... 128/898 |
| 5,383,892 | 1/1995 | Cardon et al. ............... 606/198 |
| 5,405,378 | 4/1995 | Strecker . |
| 5,449,373 | 9/1995 | Pinchasik et al. . |
| 5,456,713 | 10/1995 | Chuter . |

(List continued on next page.)

OTHER PUBLICATIONS

Endovascular and Surgical Techniques: "A Telescopic Stent–graft for Aortoiliac Implantation", T.A.M. Chuter et al., *Eur J Vasc Endovasc Surg*, vol. 13, 79–84 (1997).

"Malignant Colorectal Obstruction: Treatment with a Flexible Covered Stent", In Wook Choo, M.D., et al. *Radiology*, vol. 206, No. 2, 415–421 (Feb. 1998).

"Aortic Arch Reconstruction by Transluminally Placed Endovascular Branched Stent Graft", Kanji Inoue, M.D., et al., *Circulation*, Nov. 9, 1999, II–316–II–321.

"Transluminal Endovascular Branched Graft Placement for a Pseudoaneurysm: Reconstruction of the Descending Thoracic Aorta Including the Celiac Axis", Kanji Inoue, M.D., et al., *J Thoracic and Cardiovasc Surg*, vol. 114, No. 5, 859–861 (Nov. 1997).

"What are the Characteristics of the Ideal Endovascular Graft for Abdominal Aortic Aneurysm Exclusion?", Robert C. Allen, M.D., et al., *J Endovasc Surg* 1997; 4:195–202.

"Inoue's Endovascular Branched Stent Graft for Thoracic Aortic Aneurysms", Hiroki Hosokawa, et al., Presentation, Tenth Annual TCT, Oct. 6–11, 1998.

"Endovascular Repair of Aortoiliac Aneurysms Involving Hypogastric Arteries with Branched Stent–Grafts", Timoyuki Iwase, et al., Presentation, Tenth Annual TCT, Oct. 6–11, 1998.

International Search Report for corresponding PCT application PCT/US00/32980 (3 pages).

*Primary Examiner*—Cary E. O'Connor
(74) *Attorney, Agent, or Firm*—Popovich & Wiles, P.A.

(57) ABSTRACT

The invention provides an endovascular graft system for repair of aneurysms. The graft system includes a trunk component and first and second leg components. The graft components include graft material supported by a plurality of stents which are spaced apart and affixed to the graft material in a manner that allows articulation of the graft system without excessive wear of the graft material. The stents are formed by intersecting struts which may be tapered to relieve stress. A stabilizing mechanism is provided to stabilize the position of the legs with respect to the trunk when the graft system is deployed.

11 Claims, 26 Drawing Sheets

U.S. PATENT DOCUMENTS

| | | |
|---|---|---|
| 5,489,295 | 2/1996 | Piplani et al. . |
| 5,522,880 | 6/1996 | Barone et al. . |
| 5,545,209 | 8/1996 | Roberts et al. . |
| 5,562,726 | 10/1996 | Chuter . |
| 5,593,417 | 1/1997 | Rhodes ................... 606/191 |
| 5,597,378 | 1/1997 | Jervis ....................... 606/78 |
| 5,609,625 | 3/1997 | Piplani et al. . |
| 5,609,627 | 3/1997 | Goicoechea et al. . |
| 5,628,783 | 5/1997 | Quiachon et al. . |
| 5,653,743 | 8/1997 | Martin . |
| 5,653,748 | 8/1997 | Strecker . |
| 5,669,925 | 9/1997 | Saunders ................ 606/108 |
| 5,676,696 | 10/1997 | Marcade . |
| 5,683,449 | 11/1997 | Marcade . |
| 5,683,452 | 11/1997 | Barone et al. . |
| 5,683,453 | 11/1997 | Palmaz . |
| 5,693,083 | 12/1997 | Baker et al. . |
| 5,693,087 | 12/1997 | Parodi . |
| 5,693,089 | 12/1997 | Inoue . |
| 5,716,365 | 2/1998 | Goicoechea et al. ........ 606/108 |
| 5,723,003 | 3/1998 | Winston et al. . |
| 5,755,773 | 5/1998 | Evans et al. . |
| 5,769,887 | 6/1998 | Brown et al. . |
| 5,776,161 | 7/1998 | Globerman ................ 606/194 |
| 5,776,181 | 7/1998 | Lee et al. . |
| 5,776,186 | 7/1998 | Uflacker . |
| 5,782,904 | 7/1998 | White et al. ................. 623/1 |
| 5,782,909 | 7/1998 | Quiachon et al. . |
| 5,792,144 * | 8/1998 | Fischell et al. ............ 606/194 |
| 5,800,515 | 9/1998 | Nadal et al. . |
| 5,810,870 | 9/1998 | Myers et al. ............... 606/198 |
| 5,817,126 | 10/1998 | Imran ........................ 606/198 |
| 5,824,036 | 10/1998 | Lauterjung . |
| 5,824,037 | 10/1998 | Fogarty et al. . |
| 5,824,039 | 10/1998 | Piplani et al. . |
| 5,824,044 | 10/1998 | Quiachon et al. . |
| 5,843,158 | 12/1998 | Lenker et al. . |
| 5,843,160 | 12/1998 | Rhodes . |
| 5,843,167 | 12/1998 | Dwyer et al. . |
| 5,855,598 | 1/1999 | Pinchuk . |
| 6,013,854 | 1/2000 | Moriuchi ..................... 623/11 |
| 6,030,415 | 2/2000 | Chuter ......................... 623/1 |
| 6,039,749 | 3/2000 | Marin et al. ............... 606/198 |
| 6,039,758 | 3/2000 | Quiachon et al. . |
| 6,102,940 | 8/2000 | Robichon et al. . |
| 6,190,406 | 2/2001 | Duerig et al. ................. 623/1 |

\* cited by examiner

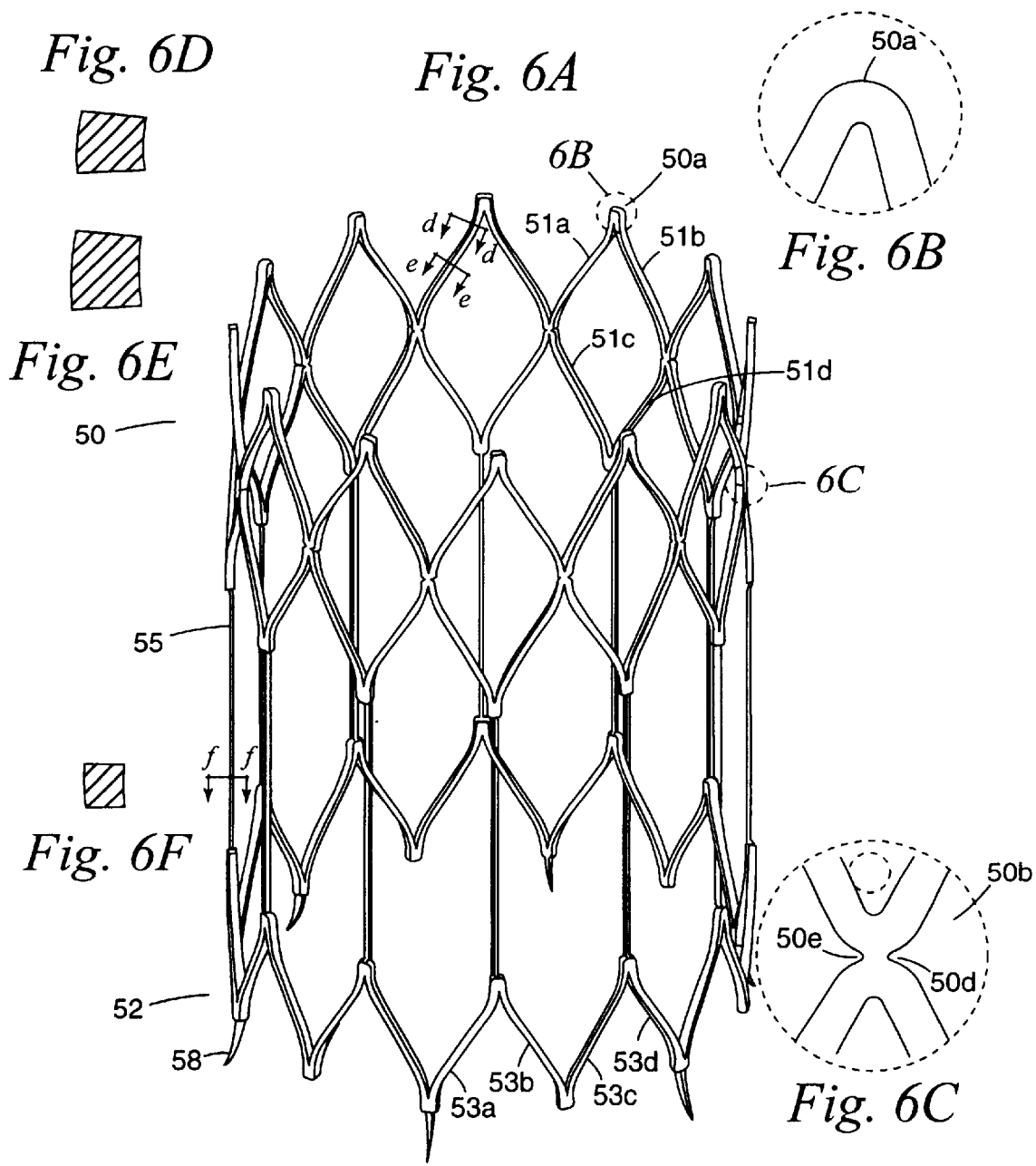

ENDOVASCULAR GRAFT SYSTEM

FIELD OF THE INVENTION

This invention relates to endovascular graft systems for the repair of aneurysms. In particular, this invention relates to an endovascular graft system for use in repairing abdominal aortic aneurysms.

BACKGROUND OF THE INVENTION

Aortic aneurysms represent a significant medical problem for the general population. Aneurysms within the aorta presently affect between two and seven percent of the general population and the rate of incidence appears to be increasing. This form of vascular disease is characterized by a degradation in the arterial wall in which the wall weakens and balloons outward by thinning. If untreated, the aneurysm can rupture resulting in death within a short time.

The traditional treatment for patients with an abdominal aortic aneurysm is surgical repair. This is an extensive operation involving transperitoneal or retroperitoneal dissection of the aorta and replacement of the aneurysm with an artificial artery known as a prosthetic graft. This procedure requires exposure of the aorta through an abdominal incision extending from the lower border from the breast bone down to the pubic bone. The aorta is clamped both above and below the aneurysm so that the aneurysm can be opened and the prosthetic graft of approximately the same size as the aorta is sutured in place. Blood flow is then re-established through the prosthetic graft. The operation requires a general anesthesia with a breathing tube, extensive intensive care unit monitoring in the immediate post-operative period along with blood transfusions and stomach and bladder tubes. All of this imposes stress on the cardiovascular system. This is a high-risk surgical procedure with well-recognized morbidity and mortality.

More recently, significantly less invasive clinical approaches to aneurysm repair known as endovascular grafting have been proposed. (See, Parodi, J. C., et al. "Transfemoral Intraluminal Graft Implantation for Abdominal Aortic Aneurysms," 5 Annals of Vascular Surgery, 491 (1991)). Endovascular grafting involves the transluminal placement of a prosthetic arterial graft in the endoluminal position (within the lumen of the artery). By this method, the graft is attached to the internal surface of an arterial wall by means of attachment devices such as expandable stents, one above the aneurysm and a second below the aneurysm.

Although endovascular grafting represents a desirable improvement over traditional surgical repair, current endovascular graft systems suffer from certain deficiencies. For example, current endovascular graft systems typically are unsuitable for use in an aneurysm which is tortuous. Aneurysms in the aorta create tortuosity as they grow. Aneurysms grow both in diameter and length, thus "pushing" the adjacent upper and lower portions of the arteries upward and downward, respectively. Since the aorta is relatively "fixed" at the renal arteries, the portion of the aorta below and near the renal arteries becomes bent and curved in order to accommodate the added length. A similar phenomenon occurs below the aneurysm in the iliac arteries, leading to tortuous iliacs. As many as 20% of aortic aneurysms may have so much tortuosity that they are unable to be fitted with an endovascular graft of this kind. Such systems are unable to conform to the curved walls of the vasculature due to the tortuosity caused by the growing aneurysm.

A specific problem is the "angulation" or bend in the neck of the aorta, where it meets the upper part of the aneurysm. This angulation may result in several problems which limit the effectiveness of traditional endovascular graft systems which do not have designs that conform to the tortuosity and angulation above the aneurysm. First, since these systems are typically anchored above the aneurysm with a stent, a portion of the stent may extend into the blood flow path, creating turbulence which may result in blood clotting. It is well-known that in coronary vessels, stents used to treat constrictive lesions must be well apposed to the wall of the vessel to prevent the possibility of thrombosis. Second, a non-conforming upper stent will not place the upper end of the graft in good apposition to the aortic wall, making it difficult to obtain a good seal with a conventional endovascular graft system. Such is illustrated in FIG. 2, showing a generic endovascular graft attached to a conventional non-conforming expanded metal stent in the neck of a tortuous aortic neck. Since this conventional stent will not conform to the tortuosity of the aorta, an upper edge 1 of the stent extends into the blood flow path increasing the chance of thrombosis. Further, a lower edge 2 is not apposed to the wall of the aorta so that the graft material 3 affixed to it does not properly seal. A third problem with nonconforming attachment systems is that once placed in tortuous or angulated aneurysmal anatomy, they are unstable and can "pop-out" of position. The attachment system shown in FIG. 2 is an example of an unstable attachment system. Conventional endovascular graft systems having an attachment system intended to project across and above the renal artery ostia also pose a different problem since the attachment system obstructs the renal arteries making it difficult, if not impossible, to effect a repair on a renal artery once the stent is in place.

Thus, a need exists for a prosthetic endovascular graft system which will permit stable conformance to bends within an aneurysm, while providing a good seal to the vasculature.

Another challenge for endovascular grafting of aortic aneurysms relates to the need for graft systems to be delivered in as small of a "profile" as possible. This has driven the design of most endovascular grafting systems to be fabricated with very thin-walled graft conduits. This thin walled conduit, usually coupled to an internal support framework, typically a metallic framework attached to the graft conduit on either the inside or on the outside, is susceptible to "wear and tear" mechanisms arising from the pulsatile blood pressure and flow in the aorta. Numerous incidences have been reported in the literature of holes and tears being created in the graft conduit from the cyclic, localized rubbing of the metallic framework against the thin walled graft conduits of a variety of endovascular grafting systems.

Thus, a need exists for a prosthetic endovascular graft system which will minimize or eliminate the wearing mechanisms on the tubular graft conduit, enabling the graft system to be safely utilized in patients for long periods of time, i.e. several years, without concern of premature failure due to wear.

Yet another concern of current endovascular graft systems relates more specifically to the long-term integrity of metallic stents which are used for supporting the structure of the graft material. Since portions of many of the stents used for graft support are in direct interface with the aorta (and iliac arteries in the case of biluminal endovascular graft systems), the pulsatile forces that cause pulsatile diameter changes on these vessels are transferred to these stent portions. This pulsation in the stents leads to cyclic stressing, and can cause premature fatigue failure and breakage.

Thus, a need exists for a prosthetic endovascular graft system which incorporates stents that are designed to minimize cyclic stresses and thus avoid fatigue failure.

SUMMARY OF THE INVENTION

This invention is an endovascular graft system for use in repairing aneurysms. In one aspect, the invention is an endovascular graft system capable of being deployed at a desired location within a vessel. The graft system includes an aortic stent having first and second ends, a trunk formed of a graft material having an interior surface defining a lumen and being affixed to the second end of the aortic stent, and a plurality of stents affixed to and supporting the interior surface of the trunk, the plurality of stents being spaced apart such that fully unsupported regions of the trunk lie between adjacent stents. The graft material of the trunk is affixed to the aortic stent and to the plurality of stents in a manner which limits movement of the graft material with respect to the aortic stent and the plurality of stents. The graft material of the trunk may be crimped toward the lumen in the unsupported regions between stents. The trunk has first and second branches configured such that the lumen comprises a main lumen and first and second branch lumens and wherein the plurality of stents includes a first or mid-stent located in the main lumen between the aortic stent and the first and second branch lumens and further includes a plurality of second stents located in the first and second lumens.

In another aspect, this invention is a stent for placement in a vessel of a patient's vascular system. The stent comprises a substantially tubular body portion having a plurality of struts, each strut having first and second ends and a midpoint located midway therebetween, each end of the plurality of struts intersecting with an end of at least one adjacent strut to form a plurality of strut intersections, at least one strut being configured to taper between the midpoint and the first and second ends in a manner that is gradual and substantially continuous. The stent has a tubular body portion which defines a longitudinal axis and has a first end and a second end. A plurality of intersecting struts adjacent the first end form a substantially diamond shape pattern at the first end of the stent and a plurality of intersecting struts adjacent the second end form a substantially zigzagged pattern at the second end of the stent. The diamond shaped pattern and zigzagged pattern are connected by a plurality of longitudinal struts which are parallel to the longitudinal axis of the stent. The strut which is configured to taper may be one or all of the struts which are adjacent the first end of the stent. The tapering strut may be configured such that the strut tapers from a larger dimension at the midpoint to smaller dimensions at the first and second ends or from a small dimension at the midpoint to larger dimensions at the first and second ends.

In another aspect the invention is a delivery catheter for delivering and deploying an endovascular graft system at a desired location within a vessel of a patient's vascular system. The catheter includes a handle and a shaft having a distal end and a proximal end, the proximal end being connected to the handle, the shaft further having an outer surface and defining an inflation lumen and a guidewire lumen. A balloon is attached at a location spaced from the distal end of the catheter. The balloon has an interior in fluid communication with the inflation lumen. A transition element is affixed to the balloon. The transition element has a distal portion between the balloon and the distal end of the catheter, the distal portion being configured to provide increasing stiffness from the distal end of the catheter to the balloon. The shaft, balloon and transition element together form a portion of an inner catheter. An outer sheath defines a lumen which contains the inner catheter. The outer sheath is configured to move from an unretracted position to a retracted position and has a distal end positioned about the balloon when in the unretracted position. The distal portion of the transition element may taper outwardly from the distal end of the catheter to the balloon. The lumen of the outer sheath has a first diameter at the distal end of the outer sheath which is less than the diameter of the balloon when inflated.

In another aspect, the invention is a delivery catheter for delivering an endovascular graft system at a desired location within a vessel of a patient's vascular system. The delivery catheter includes a shaft. First and second graft components are positioned about the shaft, the first graft component being positioned distally of the second graft component. The first graft component is configured to be deployed in the vessel prior to deployment of the second graft component. Both the first and second graft components have proximal and distal portions, the distal portion of the second graft component being configured to be deployed within the proximal portion of the first graft component. The catheter has a retractable sheath which defines a lumen containing the shaft and the first and second graft components. The sheath is configured to deploy the first graft component when it is withdrawn a first distance and to deploy the second graft component when it is withdrawn a second distance. Means are included for stabilizing the position of the distal portion of the second graft component with respect to the proximal portion of the first graft component when the sheath is being withdrawn the second distance.

In a further aspect the invention is a delivery catheter for delivering an endovascular graft system at a desired location within a vessel of a patient's vascular system. The delivery catheter includes a handle and a shaft connected to the handle. First and second graft components are positioned about the shaft, the first graft component being positioned distally of the second graft component. The first graft component is configured to be deployed in the vessel prior to deployment of the second graft component. The first and second graft components each have proximal and distal portions, the distal portion of the second graft component being configured to be deployed within the proximal portion of the first graft component. The distal portion of the second graft component has a fastening element. A retractable sheath defines a lumen which contains the shaft and the first and second graft components. The handle is configured to retract the sheath to deploy the first graft component when the sheath is retracted a first distance and to deploy the second graft component when the sheath is retracted a second distance. A stabilizing element connected at one end to the handle and at another end to the fastening element of the second graft component stabilizes the second graft component with respect to the first graft component during deployment. The handle, stabilizing element and fastening element are configured such that the stabilizing element is retracted in a manner that disconnects the stabilizing element from the fastening element when the second graft component is deployed. The second graft component includes a stent located at the distal portion which has an eyelet comprising the fastening element. The stabilizing element may be a wire.

BRIEF DESCRIPTION OF THE DRAWINGS

FIG. 6A is a perspective view of the aortic stent of this invention. FIGS. 6B and 6C show enlarged views of portions of the stent, and FIGS. 6D, 6E, and 6F show details of the cross-sectional shapes of various portions of the stent shown in FIG. 6A.

DESCRIPTION OF THE PREFERRED EMBODIMENTS

Figure 1:
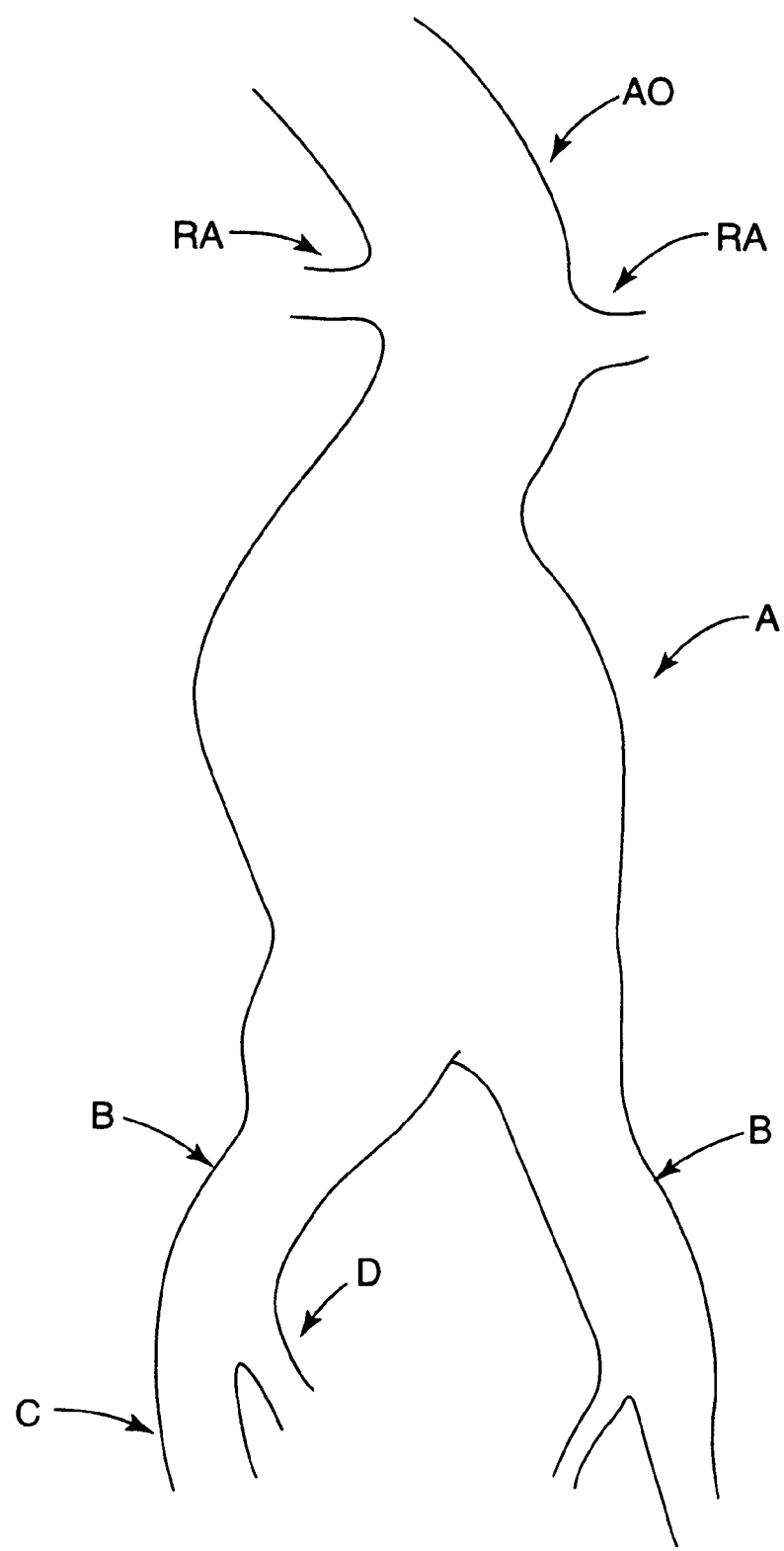
FIG. 1 is a diagrammatic view of a portion of a human vascular system depicting an abdominal aortic aneurysm which extends from below the renal arteries and into the common iliac arteries and which has caused angulation of the aorta above and below the renal arteries.

The terms "distal" and "proximal" as used in this specification refer to the method of delivery of the graft system, not to the vasculature. The preferred method of this graft system contemplates advancement of a catheter in a retrograde manner (i.e., against the flow of blood). Therefore, "proximal" refers to a location closer to the physician and "distal" refers to a location farther from the physician. The vasculature is referred to with respect to the cranial (closer to head) and caudal (closer to feet) directions. Also, as used in this specification, the term "above", in the context of relative positioning with respect to the aneurysm, refers to the region cranial of the aneurysm, for example, within the aorta, whereas "below" refers to the region of the vasculature caudal of the aneurysm, for example, within the common iliac arteries.

The present invention is a graft system for implantation within a lumen in a patient's body. Although the specific embodiments disclosed herein relate to an endovascular graft system for treating a variety of abdominal aortic aneurysms, it will be understood that the graft system will have a broader application and is suitable for use in any body lumen which may be repaired or reinforced by a graft system.

The endovascular graft system of this invention may be useful for treating a variety of aneurysms. For example, a biluminal endovascular graft system may be used for treating aneurysms that extend close to or into the common iliac arteries. In these aneurysms there is not a suitable place within the aorta to seat the lower end of a simple tubular graft. Therefore, the graft must be able to extend into each iliac artery for suitable seating. By "seating" it is meant that the graft is implanted, fixed, or otherwise secured to the vasculature.

The graft of the preferred embodiment is supported internally by individual stents, or support stents, which are themselves connected to the graft in a manner which secures their position, for example, by sutures. This endovascular graft system is envisioned for use primarily with aneurysms which would benefit from treatment with a biluminal multicomponent endovascular graft system. That is, such a graft system has an aortic stent capable of fitting into the neck of an aorta which has been bent or angulated as a result of an aneurysm. A trunk extends from the aortic stent into the aneurysm. The trunk splits into two branches into which right and left legs are secured during deployment of the graft system across the aneurysm. The right and left legs have iliac stents at their proximal ends for connection with a respective common iliac artery. However, depending upon the geometry of the aneurysm, this system could be useful in other graft system designs such as with a unibody bifurcated graft; a tube graft; or a modular two-piece graft having one short segment and one long segment extending from the main body of the graft, and a separate leg which can be joined to the short segment, as is known to one of skill in the art.

Turning now to the Figures, the shape of an aneurysm and the placement and use of the endovascular graft system are described.

FIG. 1 depicts an aneurysm A in the infrarenal aorta which extends into the common iliac arteries. Aneurysm A has caused aorta Ao to become bent or angulated. The infrarenal aorta is that portion of the aorta disposed between the left and right renal arteries RA and the common iliac arteries B that branch left and right. No distinction is made in the figures between elements introduced on the left or the right of the patient's vasculature. Each common iliac artery branches into internal and external iliac arteries, D and C respectively. External iliac artery C becomes the femoral artery below the inguinal ligament. Internal iliac artery D is also known as the hypogastric artery.

Figure 3A:
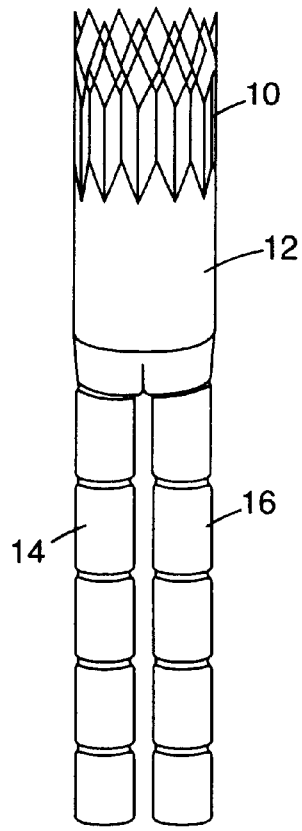
FIG. 3A is a perspective view of a biluminal endovascular graft system of this invention and FIG. 3B is a detailed perspective view of the aortic stent, trunk, and branches of the biluminal graft system of FIG. 3A.
Figure 4:
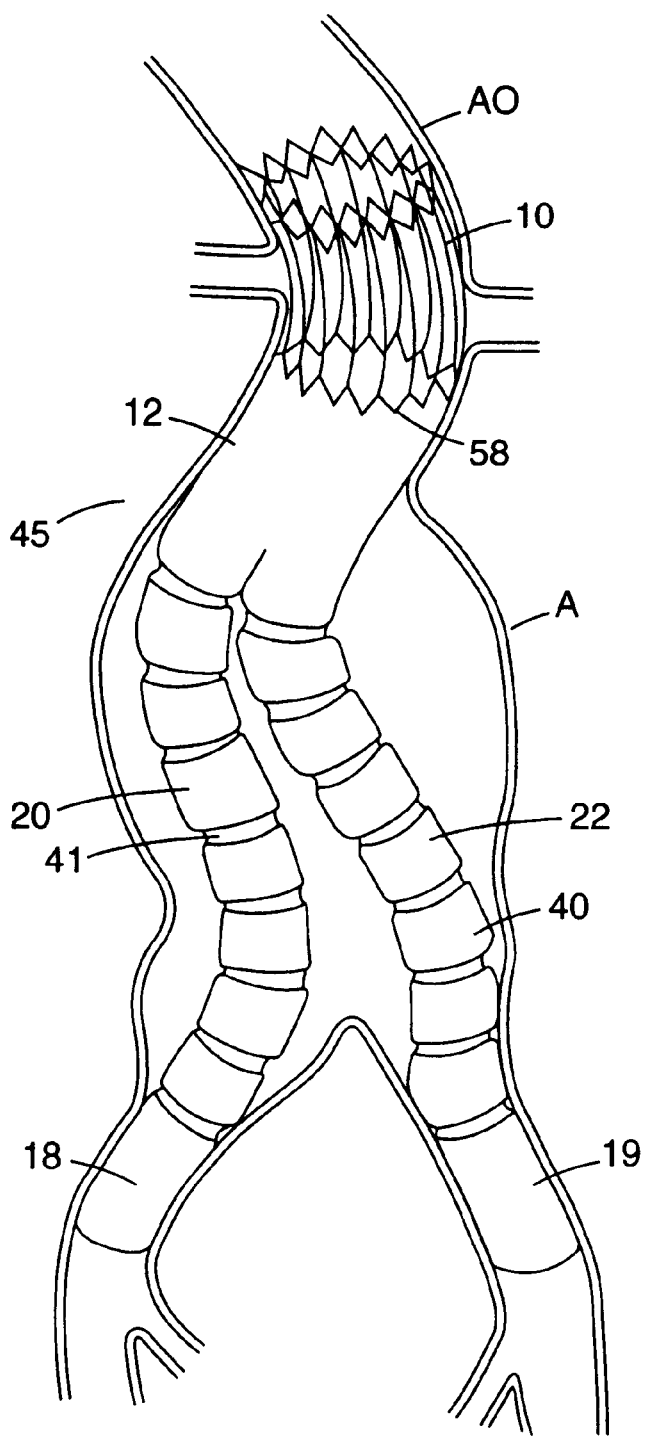
FIG. 4 is a view of the aneurysm of FIG. 1 with the fully deployed biluminal graft system of FIG. 3 in place.

FIG. 3A illustrates a biluminal endovascular graft system of the present invention. Aortic stent 10 is shown connected to graft material 45 forming trunk 12 having two branches 14 and 16. Trunk branches 14 and 16 are designed to join with legs 15 and 17, respectively, thus forming a biluminal endovascular graft system. Legs 15 and 17 are designed to be positioned within branches 14 and 16. In a preferred embodiment, the branches overlap the legs at least about 1.5 cm. Once positioned, branch 14 and leg 15 form conduit 20 and branch 16 and leg 17 form conduit 22 as best seen in FIG. 4. The friction of the overlap between the legs and branches keep conduits 20 and 22 from coming apart. At the caudal or proximal end of legs 15 and 17 are positioned iliac stents 18 and 19. Iliac stents 18 and 19 are sutured within an elongated portion of the conduits at the caudal ends thereof and are sized such that when expanded will fix the ends of the conduits within the iliac arteries.

Figure 3A:
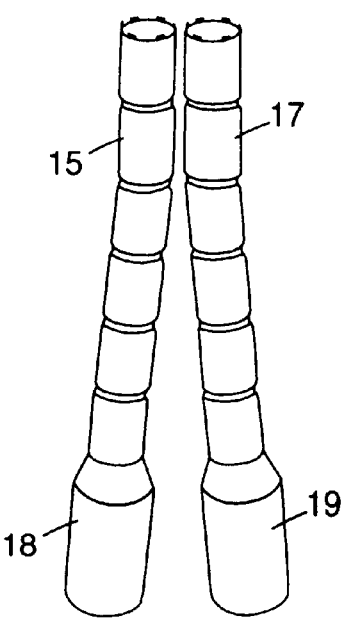
Figure 3B:
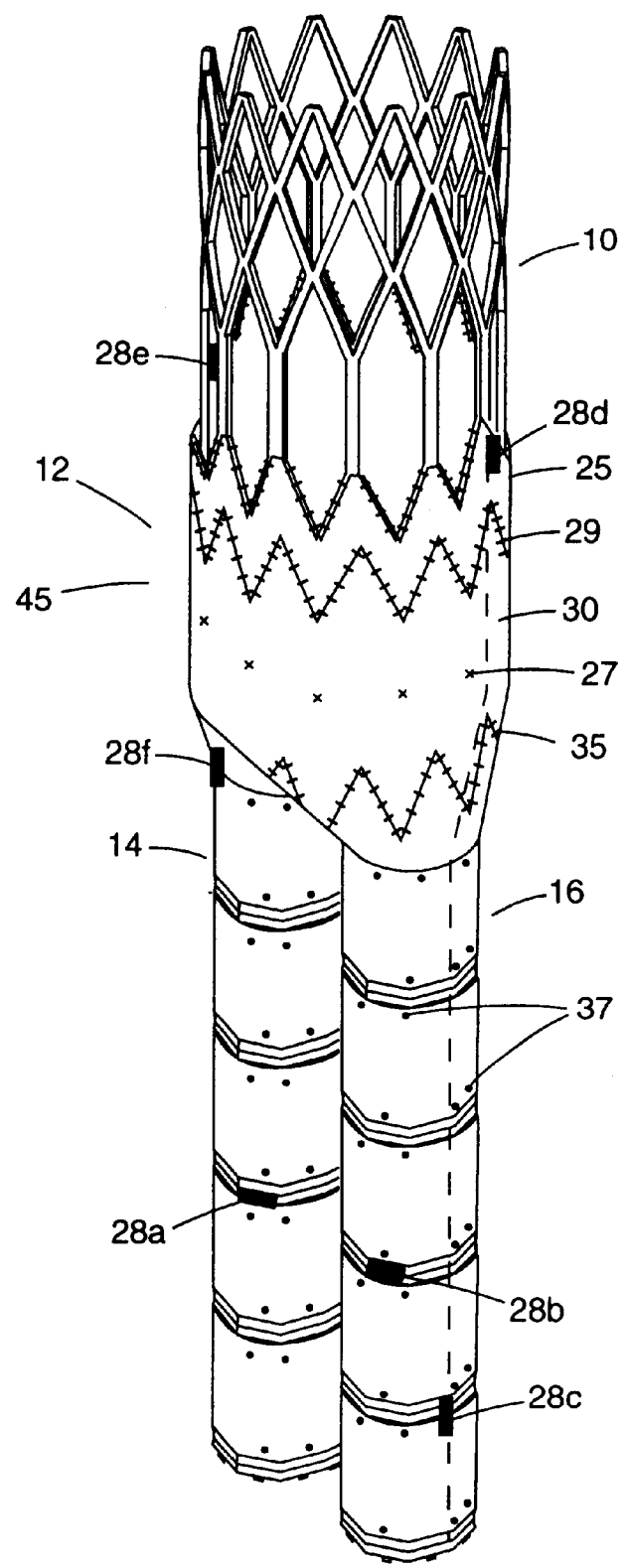

FIG. 3B illustrates in greater detail the aortic stent, the trunk and its branches. FIG. 4 shows the fully deployed graft system. FIG. 3B shows that graft material 45 of trunk 12 is joined to aortic stent 10 via sutures, shown here as blanket stitches 25. Mid-stent 30 (not visible within the graft material making up trunk 12) is stitched to trunk 12 via blanket stitches 29 and 35. Point stitches 27 secure the struts of mid-stent 30. Trunk 12 (having branches 14 and 16) with stent 10 comprises a first component of the deliver system. Legs 15 and 17 comprise second and third components of the delivery system. Two components of the delivery system (trunk 12 and branches 14 and 16 along with stent 10 and leg 15) are loaded into a single delivery catheter and delivered through one femoral artery into the aorta. Trunk 12 and leg 15 are spaced apart and positioned sequentially in the delivery catheter. Aortic stent 10 is moved into the desired position, typically across the renal artery ostia. The catheter is manipulated to withdraw an outer sheath which exposes the aortic stent and allows it to expand radially so that it seats within the aorta. Further retraction of the outer sheath allows trunk 12 with its branches 14 and 16 to expand fully. Right leg 15 of the system is then positioned within the trunk branch 14 and delivered from the same delivery catheter, thus forming conduit 20. The third component of the delivery system, left leg 17, is delivered by means of a separate delivery catheter from the other femoral artery, up the iliac artery and into branch 16 of the trunk. Conduit 22 is thus formed and is identical in structure to conduit 20. The length of the overlap between the branches and legs can be varied by the physician as the system is delivered. Thus, the length of the system can be customized to the patient. Radiopaque markers 28d, 28e, and 28f help position the upper end of trunk 12 to facilitate proper position and orientation in the aorta, relative to the renal arteries. Marker 28f is positioned at the upper end of branch 16 (the ipsilateral branch) to indicate the maximum overlap position for legs 15 and 17, so as to prevent excess overlap, or "stove-piping". Markers 28a, 28b, and 28c are positioned approximately 2 cm above the caudal end of the branches 14 and 15. This allows legs 15 and 17 to be positioned with at least a minimal amount of overlap. Marker 28c is positioned near the outer aspect of the caudal end of branch 16 (the contralateral branch), to facilitate advancement of a wire and contralateral delivery system into that branch.

FIG. 4 illustrates the biluminal endovascular graft system fully deployed across an aortic aneurysm. Aortic stent 10 is shown conforming to the curvature of the aorta. The femoral artery is entered within the thigh by an arterial incision where the vessel is close to the undersurface of the skin. A guidewire is first endoluminally placed, using conventional techniques to a position in the patient's thoracic aorta, above an aortic aneurysm such as depicted in FIG. 1. The delivery system is guided into the aneurysm along this guidewire. The guidewire remains in a fixed position throughout the endoluminal procedure. Conventional angiography techniques are employed to identify the aneurysm and the position of key anatomical structures such as the renal and hypogastric arteries. The components to be delivered in this manner are in a compressed and folded state in the delivery catheter. That is, the material making up the graft system is maneuvered into position and then allowed to expand as described below. The delivery system is described in greater detail below with respect to FIGS. 12–18.

Figure 5:
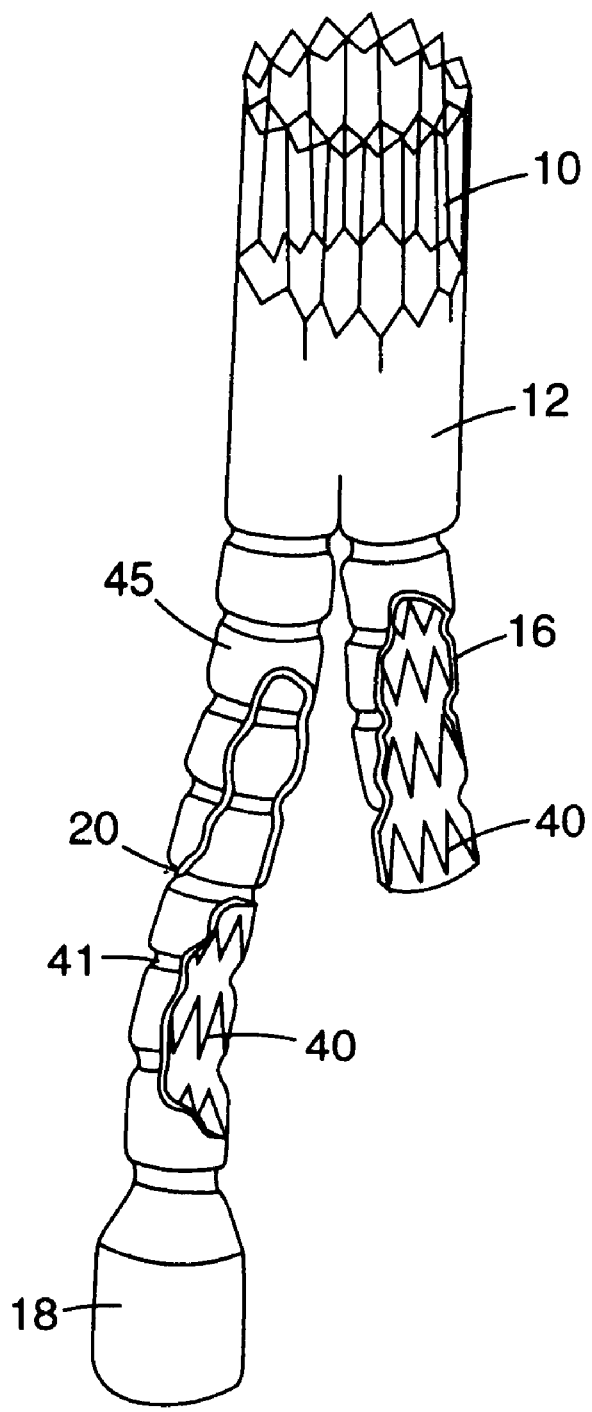
FIG. 5 is a cut-away view of a portion of the biluminal endovascular graft system of FIG. 3 showing support stents inside the conduits of the endovascular graft system.

FIG. 5 illustrates the endovascular graft system with portions cut away to show the internal structure of conduit 20 and branch 16 descending from trunk 12. The graft system includes support stents 40 within conduits 20 and 22. Typically, these support stents are relatively short compared to the total length of a leg. The size and spacing of the support stents allows for articulation of the legs of the endovascular graft system without the formation of kinks. In addition, the graft has crimps 41 formed in the spaces between the individual stents in fully unsupported portions of graft material. These crimps act as controlled bending points for the graft, while the individual support stents 40 hold open the lumen adjacent the crimps 41. Thus, the legs are able to bend or elongate to accommodate bends within the aneurysm and iliac arteries, while maintaining a large open lumen. The support stents are affixed to graft material 45 by sutures, not shown in FIG. 5.

The individual components of the implanted endovascular graft system are described in further detail below.

Aortic Stent

Figure 6G:
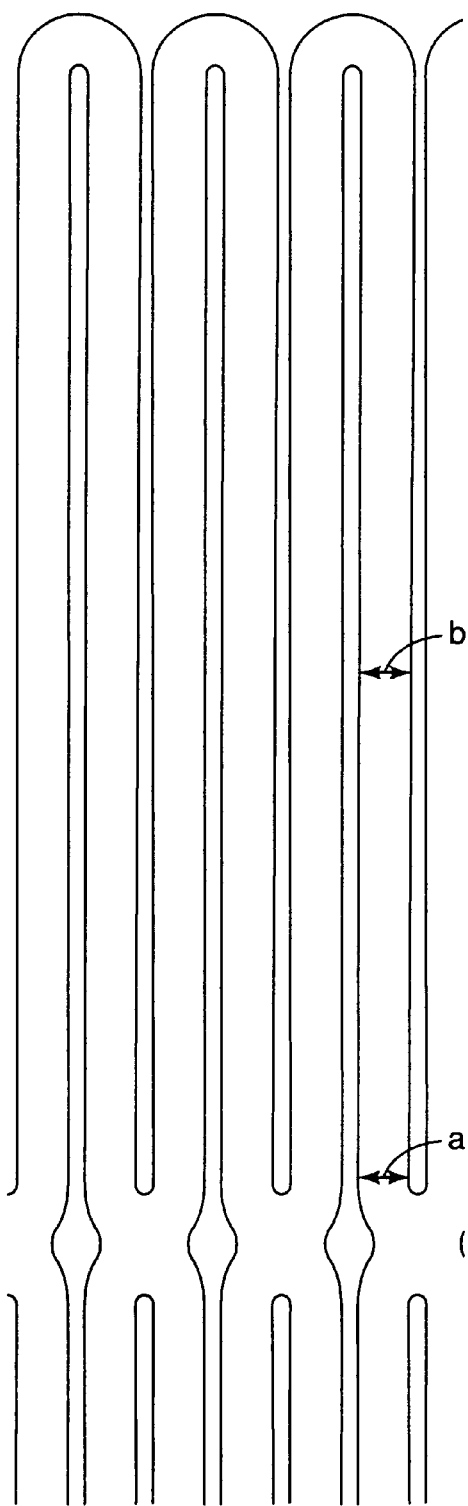
FIGS. 6G and 6H show enlarged partial views of the stent of FIG. 6A in its unexpanded condition.
Figure 6H:
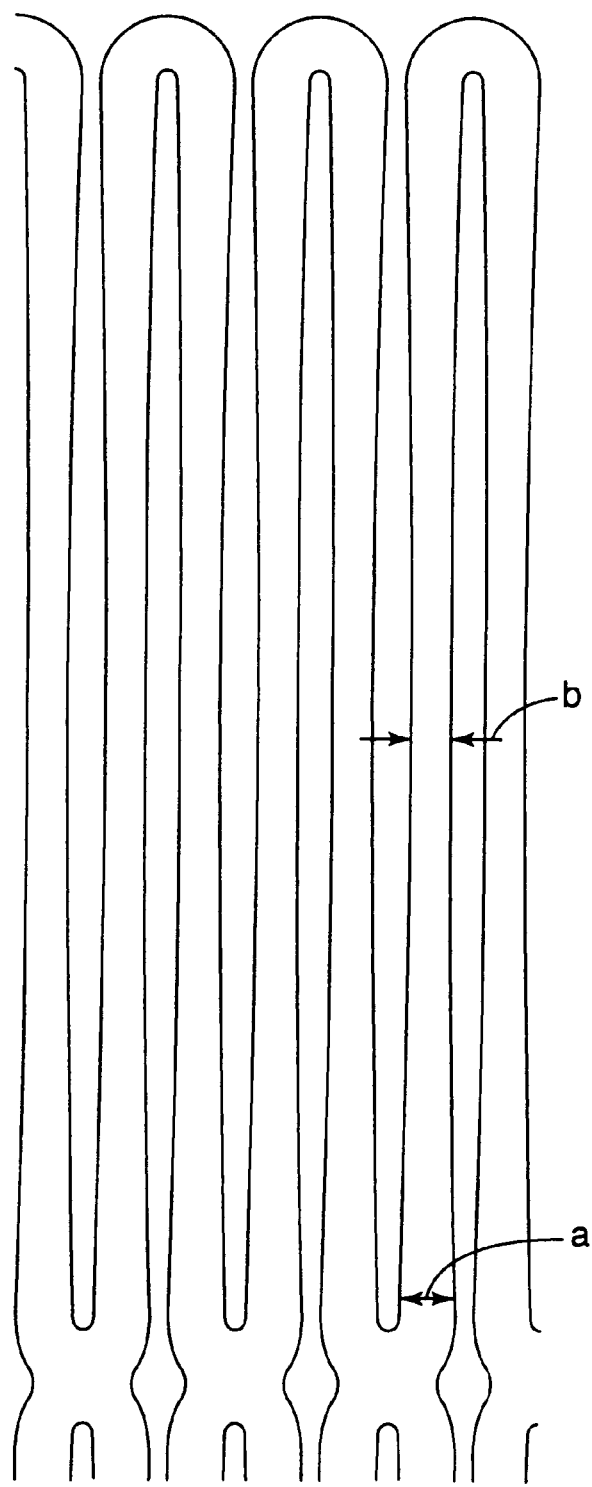
Figure 6I:
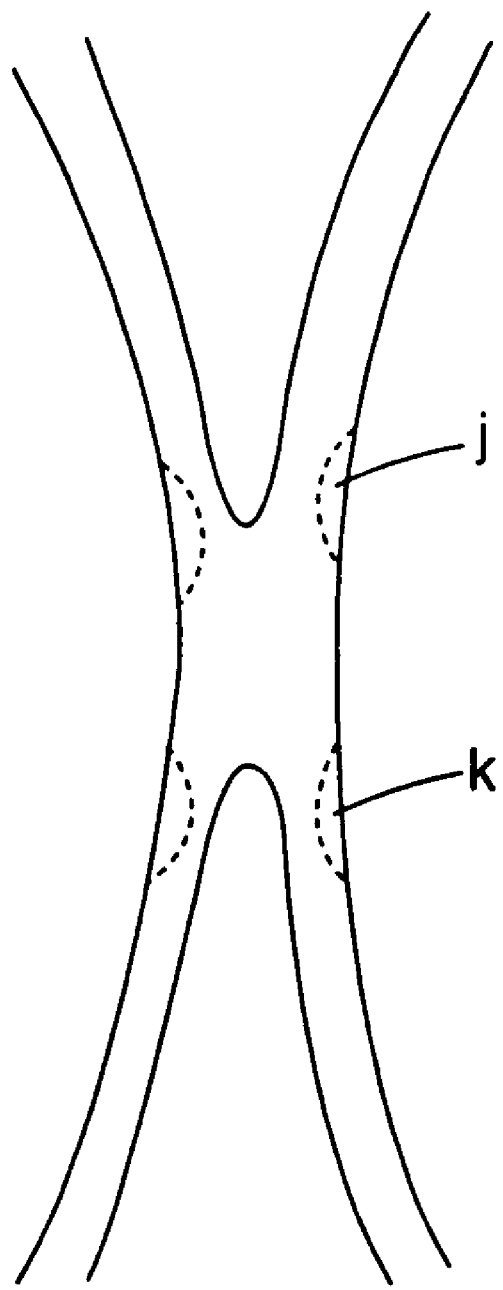
FIG. 6I shows an enlarged partial view of a prior art stent.

Aortic stent 10 shown in FIGS. 6A–6H is comprised of multiple intersecting struts configured so that there are radially strong cranial and caudal zones 50 and 52 at either end, as depicted in FIG. 6A. FIGS. 6B and 6C show enlarged views of portions of the stent. FIGS. 6D, 6E, and 6F show details of the cross-sectional shapes of struts in various portions of stent 10 along lines d—d, e—e, and f—f, respectively. These zones are configured to permit radial expansion and contraction, as described further below. The cranial and caudal zones are configured and made of materials that exhibit sufficient radial outward force or radial strength when expanded so that the graft system will be securely anchored within the aorta above the aneurysm when the stent is deployed. FIG. 6I shows an enlarged portion of a prior art stent with high stress areas.

Figure 11A:
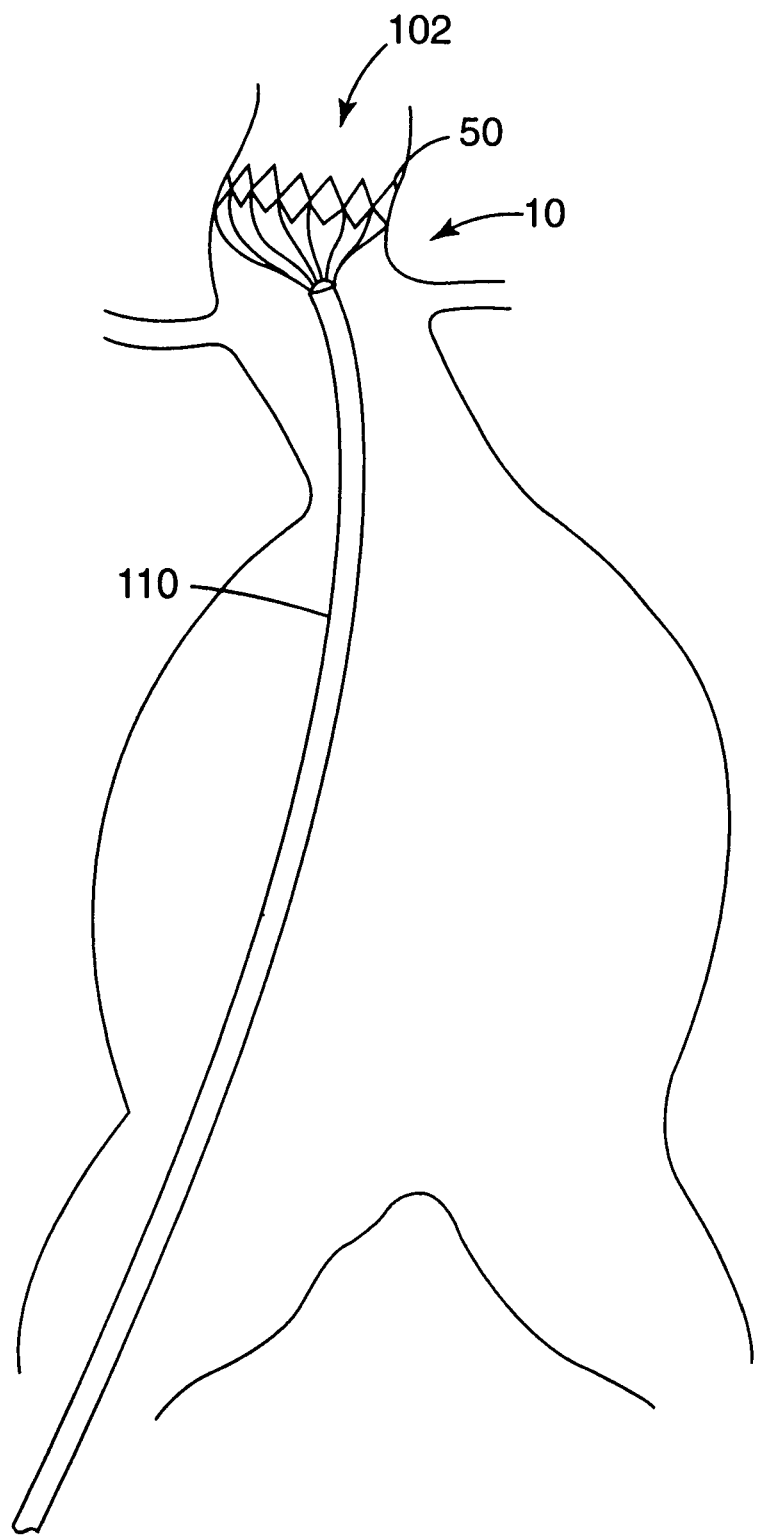
FIGS. 11A and 11B show steps in the deployment of the aortic stent of the present invention in an angulated aorta.

The cranial and caudal zones of the aortic stent are connected by an intermediate zone comprising multiple longitudinal struts 55 which are substantially parallel to a longitudinal axis defined by the tubular aortic stent. This unique three zone configuration of the aortic stent member is important for several reasons. First, this configuration allows the cranial zone of the stent to be deployed virtually independently of the caudal zone. This is illustrated best by reference to FIGS. 11A and 11B which show deployment of the aortic stent portion of the graft system in the aorta. For purposes of clarity, the guidewire which would be present during deployment is not shown. In FIG. 11A the sheath of delivery catheter 110 has been partially withdrawn to deploy cranial zone 50 of stent 10. Cranial zone 50 can be seen to be securely deployed and seated within the aorta At this stage of the delivery process blood flowing in the aorta in the direction of arrow 102 is not occluded. Thus, cranial zone 50 has been deployed and seated within the aorta in the absence of force in the direction of arrow 102 which would be exerted had the blood flow been occluded. As a result, cranial zone 50 is deployed precisely where intended.

Figure 11B:
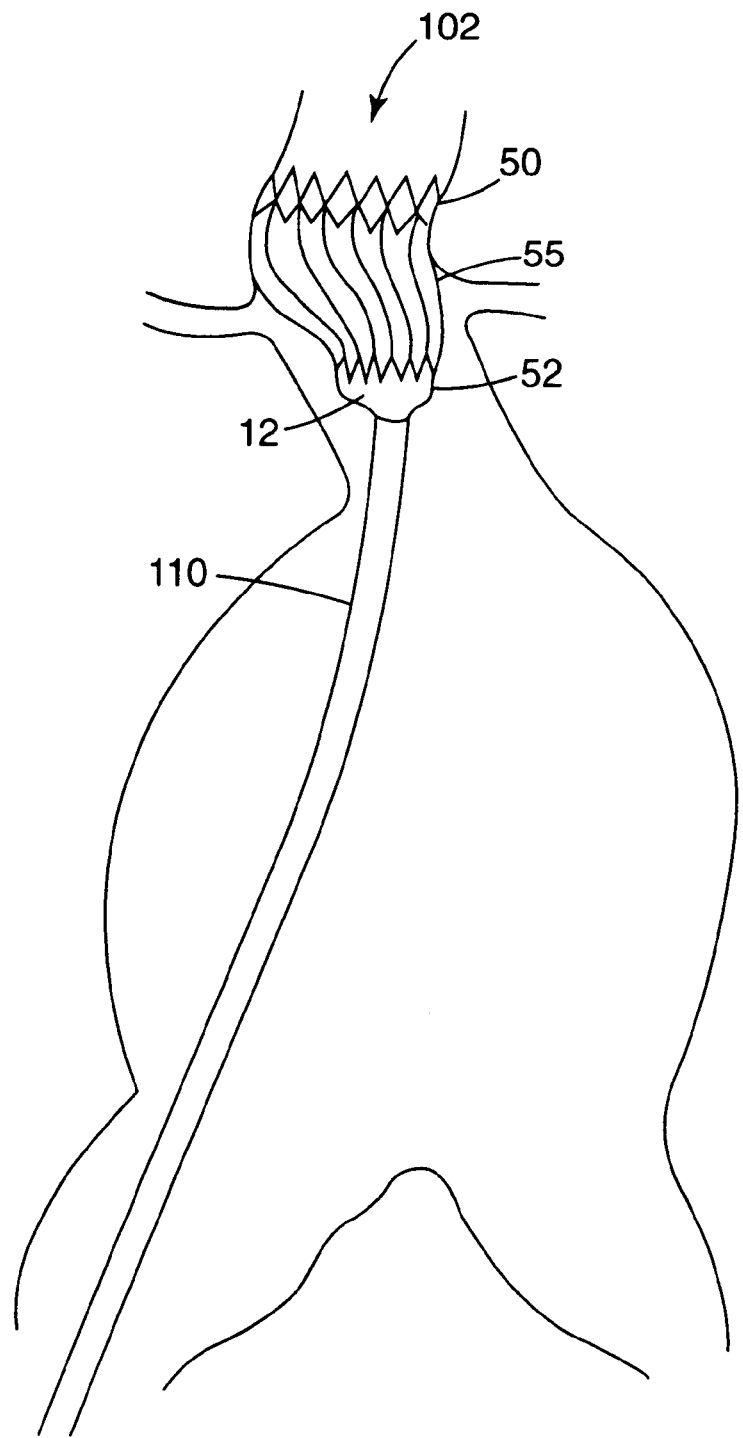

FIG. 11B shows a further stage of deployment after the sheath has been withdrawn past caudal zone 52 partially exposing the graft material of trunk 12. Caudal zone 52 is partially deployed as is trunk 12. It can be seen that the deployment of caudal zone 52 and trunk 12 has partially occluded the aorta. A force in the direction of arrow 102 begins to be asserted against the graft system and increases as caudal zone 52 and trunk 12 expands nearer the wall of the aorta. The position of the stent is, however, unaffected by that pressure since the cranial zone 50 of the stent has already been fully and securely deployed in the aorta before any significant pressure caused by occluding the aorta has built up.

This constitutes a significant advantage over current graft systems which utilize traditional self-expanding stents to secure the graft system in the aorta above the aneurysm. Stents used in those systems are relatively short, i.e., approximately 2 cm. Since the upper or cranial end of these stents cannot be deployed independently of the lower or caudal end, the result is that the stent is not seated sufficiently upon deployment before the aorta is occluded, creating a large downward force on the partially deployed graft system. Thus, the pressure caused by occlusion of the aorta makes it difficult to properly position such graft systems at a desired location with the aorta.

Figure 2:
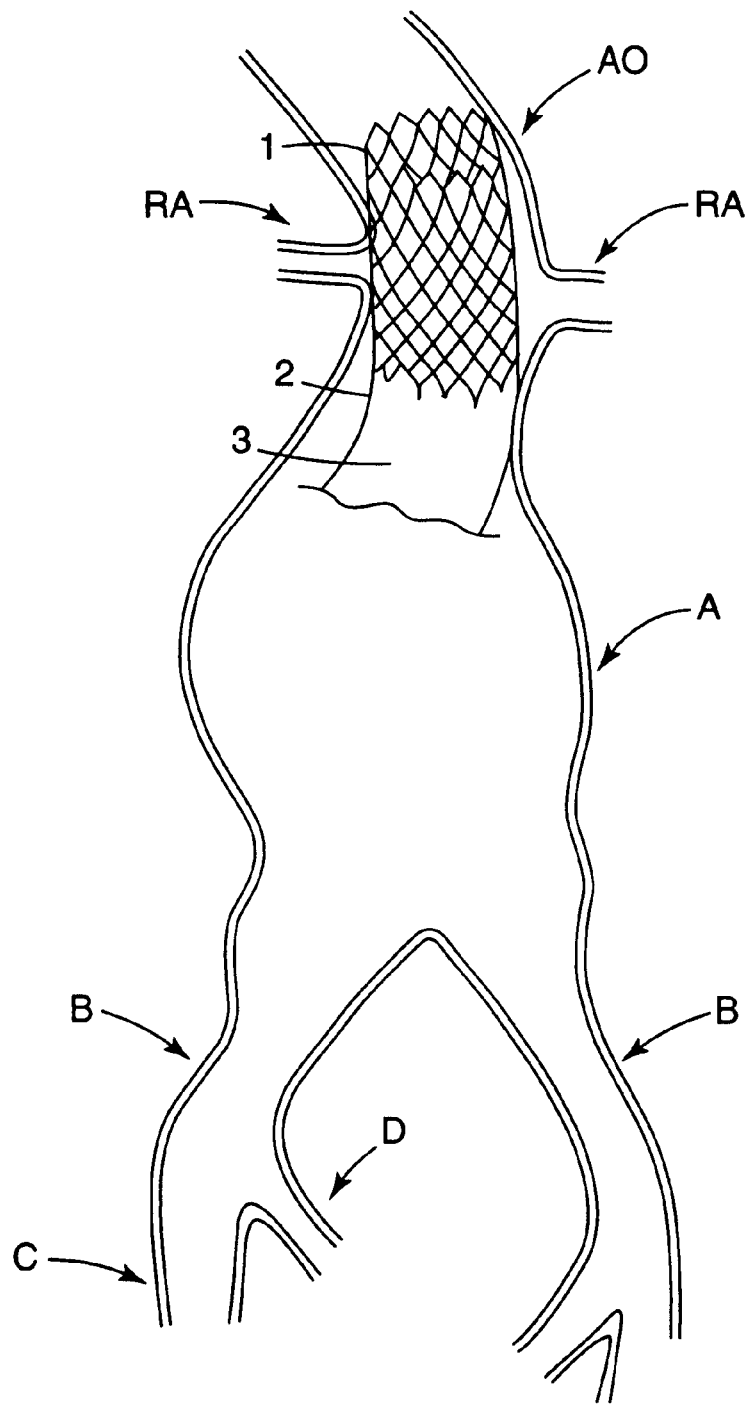
FIG. 2 is a partial view of a conventional Prior Art endovascular graft system deployed in an angulated aorta such as shown in FIG. 1.

Another advantage of the three-zoned stent is that the longitudinal struts of the transition zone between the cranial and caudal zones allow the stent to adapt to angulation or tortuosity of the aorta and still provide a good seal with the wall of the aorta Just as the quarters at each end of a stack of quarters will remain parallel even if the stack is off-set so will the cranial and caudal zones of the stent remain parallel even though the stent is deployed in a curved or tortuous aorta as in FIG. 4. In contrast, traditional stents tend not to adapt well to tortuous configurations and do not seal well against the walls of the aorta, as shown in FIG. 2.

A still further advantage of the three zoned stent is that it resists longitudinal stretching. Thus, proper positioning upon deployment is easier since the stent will not vary in length during or after delivery by the surgeon.

The longitudinal struts 55 are sufficiently flexible so that they can bend, but they do not elongate axially. The radial strength of the region of the longitudinal struts is lower than the radial strength of the caudal or cranial zones due to the configuration of the aortic stent. Radial strength is the force exerted outward (i.e., from the center of the stent) by the cranial and caudal zones and the intermediate zone. That is, these different areas exert radial forces on the vasculature when placed across the aneurysm.

The aortic stent is preferably self-expanding and is comprised of a shape memory alloy, such as that described below. The system typically is fabricated by laser cutting a tube of shape memory alloy, then forming the tube to the desired shape.

As illustrated in FIGS. 6D, 6E, and 6F, the thickness and width of longitudinal struts 55 is less than that of the struts making up the caudal or cranial zones. In this manner, longitudinal struts 55 are flexible and conformable and do not interfere with the caudal and cranial zones' ability to expand independent of each other. The longitudinal struts maintain a constant distance between the caudal and cranial zones with the result that these zones remain substantially parallel to one another even when the aortic stent is bent. Thus, the aortic stent is able to conform to the shape of a tortuous aortic aneurysm and remain longitudinally stable. Conventional stent designs which allow bending such as a coil stent or articulation also allow the stents to readily elongate. In this invention, the stent does not elongate, thus keeping the graft secure once it is placed into the vasculature.

Aortic stent 10 is sized to fit the aorta Large diameter aortas will require a larger sized graft system, and small diameter aortas will require a smaller sized graft system. For example, for a 22 to 27 mm aorta, the stent diameter is preferably 30 mm in diameter. The following preferred dimensions for the aortic stent are intended for a 30 mm diameter device. It is understood that smaller or larger diameter graft systems would require appropriately larger or smaller dimensions.

In a preferred embodiment, cranial zone 50 has diamond-shaped cells (i.e., two connected "zigzags") formed from, for example, cranial struts 51*a*, 51*b*, 51*c*, and 51*d*, and caudal zone 52 has a zigzag shape made up of caudal struts, for example, 53*a*, 53*b*, 53*c*, and 53*d*. First apex 50*a* of a diamond-shaped cell formed at the intersection of struts 51*a* and 51*b* is shown in detail in FIG. 6B. Apex 50*a* is a smooth, uniform width curved region. This shape is cut directly into the stent during the initial laser cutting, and is maintained during all subsequent processes of grit blasting, shape setting, and electropolishing (all described in further detail below). Junction 50*b* occurs at the intersection of four cranial struts. Preferably, the junction of struts is provided with indentations 50*d* and 50*e*, as shown in FIG. 6C. Second apex 51*b* joins longitudinal strut 55.

Because the aortic stent is larger in its relaxed diameter than the diameter of the aorta, there are residual stresses within the struts of the stent. Also, because the aortic stent rests directly against the aorta, any pulsatile motion of the aorta wall is transferred to the stent. This constitutes a cyclic fatigue stress that is placed on regions of the stent. In particular, in the regions of the stent near these intersections, as shown in detail in FIGS. 6B and 6C, have the highest stresses. To minimize the stresses in these regions, the intersecting regions are designed to maintain uniform beam widths near where the struts intersect. Beam width refers to the width of the strut. Indentation 50*d* is laser cut into junction 50*b* to maintain a uniform beam width in the area subject to the highest stress. By designing the junction between cells in the cranial zone to maintain uniform beam widths, the stress and strain that would normally build up in a concentrated spot near the junctures is allowed to "spread out" into the connecting regions, thereby lowering the peak values of the stresses and strains in the stent structures. In prior art stents without such indentations such as shown in FIG. 6I high stress areas j and k can occur.

To further minimize the maximum stresses in the struts of the aortic stent, the struts can have a tapering width. In one embodiment, the strut can become wider as it approaches an intersection. This is shown in FIG. 6H. The strut width near the intersections (width a) is preferably 0.025 cm (0.010 inches), and gradually tapers to a dimension of 0.0178 cm (0.007 inches) in the mid region of the strut (width b). By tapering the strut widths, the stresses in the struts adjacent the intersections is spread out further away from the intersection. The tapering of the strut widths is accomplished during laser cutting of the initial tube. By tapering the struts in this fashion, there is a trade-off, however. The tubular stent structure becomes less resistant to localized deformations, caused for example, by a protrusion within the vessel lumen. This localized deformation leads to a local torsional twisting of some of the struts, and therefore, since the struts in this case have a significant portion of their length of reduced width, the torsional rigidity is lowered.

If maximizing the resistance to localized deformation is preferred, the struts are preferably maintained at a uniform width, or most preferably actually have a reverse taper, as is shown in FIG. 6G, wherein the distance a is less than the distance b. For example, the width of cranial strut 51*a* nearest junction 50*b* is about 0.003 cm (0.001 in.) less than the width of the remainder of cranial strut 51*a*. Preferably, the strut narrows near any intersection. This is also referred to as a "reverse tape", and is shown in FIG. 6G. For the aortic stent, the reversed tapered struts are preferably about 0.025 cm (0.010 in.) wide near the intersections, and 0.028 cm (0.011 in.) wide near the middle of the strut. While this reverse taper actually tends to increase the stresses somewhat near the intersections, this increase is very small, relative to the decrease in stresses gained by having the side indentations at the intersections, as shown in FIG. 6C, as well as the uniform width connections as shown in FIG. 6B. And since the reverse taper serves to increase the torsional rigidity of the strut, the stent structure resists local deformation, and tends to maintain a circular tubular geometry, even if the lumen it is placed within is non-circular.

By minimizing the stresses in the aortic stent, the risk of fatigue fracture of the struts is greatly reduced. This lowered stress design also enables the aortic attachment system of the current invention to be utilized in a wider range of aorta sizes, and in aortas that may have high pulsatile diameter variations, while minimizing any increase in stress in the member. Additionally, when the aortic stent is designed to minimize stresses, any dimensional variations caused by processing variations in the laser cutting, grit blasting, or electropolishing (described below) will result in higher local stresses and strains, but these higher stresses and strains will still be below critical levels which could cause premature fracture of the structure.

An example of the dimensions of an aortic stent useful in this invention is one in which the cranial zone is approximately 15 mm long, and the caudal zone is approximately 7.5 mm long. Each zone preferably has 14 complete zigzags. Longitudinal struts 55 are approximately 15 mm in length. There are preferably 14 longitudinal struts, corresponding to the number of zigzags of the caudal and cranial sections. Approximately 14 mm of the length of the struts 55 are transitioned to a reduced thickness and width. Caudal and cranial zones 50 and 52 have strut thicknesses and widths between approximately 0.023 and 0.035 cm (0.009 in. and 0.014 in.) with gradual tapering strut widths as described above. In a preferred embodiment, the struts are narrower near intersections and wider in the middle of a strut, as illustrated in FIG. 6G. The reduced regions of longitudinal struts 55 have strut width and thicknesses between approximately 0.018 and 0.028 cm (0.007 and 0.011 in.) The reduced regions of longitudinal struts 55 have their widths cut to a thinner dimension directly from the laser cutting process on the initial tube. However, in the thickness direction, the laser cut tube is subsequently placed on a support mandrel and is either centerless ground or center-ground with methods known to those skilled in the art.

Stent 10 is approximately 3 cm in length. It typically is desirable to "oversize" the stent to assure a good seal and engagement within the aorta. A minimum of about 3 to 4 mm oversize is preferred. It is also expected that tissue ingrowth occurs faster with an exposed stent (as opposed to a stent covered with graft material), leading to long-term anchoring of the stent. Barbs 58, hooks, or the like may be used to increase the mechanical fixation of the stent to the aorta. If barbs 58 are used, they are preferably placed at the caudal end of the stent, as shown in FIGS. 3 to 6A. However, they could also be placed at the cranial end. The barbs are preferably sharpened on the end that engages the aorta.

For many aneurysms it is necessary to position the aortic stent across the renal arteries in order to properly anchor the system. Although this may be a desirable way to position an aortic stent to ensure that it is properly secured within the aorta, such positioning can inhibit blood flow into the renal arteries. The aortic stent of this invention crosses the renal artery without significantly inhibiting blood flow. Both the design of the stent and the small cross-sectional area of the struts prevent significant obstruction of blood flow. This minimizes thrombosis and, additionally, provides for subsequent access to the renal arteries.

The aortic stent of this invention conforms to a bend or tortuosity in the vessel and does so without any elongation in the stent. That is, it maintains longitudinal integrity unlike a coil or other stents which may bend, but also which can elongate. This is important because the aortic stent must stay in the desired position, maintain the seal with the vasculature and prevent the graft from moving axially.

When deployed, the caudal and cranial zones of the aortic stent lie against the wall of the vasculature and produce a good seal. The material in these zones is shaped to permit radial expansion and contraction of the system to conform to the size and shape of the aorta and still maintain sufficient radial force to securely anchor the graft system. This shape also permits the caudal and cranial ends of the aortic stent to expand to different diameters. This is an advantage for an aneurysm exhibiting tortuosity. The ability of the stent to conform results in good seating of the stent in the vasculature so that it cannot move out of position. In addition, the ends of the aortic stent do not rest away from the aortic wall as in prior art devices (such as that illustrated in FIG. 2). This can prevent the proper sealing of such graft systems and result in thrombosis. It is also contemplated that the objectives of the present invention can be achieved with a stent made up of multiple zones of high radial strength (such as the cranial and caudal zones) connected by multiple zones of longitudinal struts (such as the intermediate zone).

A further advantage of the present invention is that the longitudinal struts separating and joining the caudal and cranial zones can be moved out of the way in the event that further surgery on the renal arteries becomes necessary. This reintervention would be very difficult with the aortic stent of a conventional endovascular graft system in place across the renal arteries. Such systems typically have too many struts to allow them to be moved out of the way for catheters to pass into the renal arteries Even in the case where the present stent is comprised of longitudinal struts which are not of reduced thickness or width, they can be easily displaced because of their relatively long length compared to the length of the caudal or cranial zones.

Yet another advantage of the aortic attachment system of this invention is that there is a lower risk of thrombosis. This is because there is less metal and stent structure across the renal arteries than with conventional expanded metal stents.

Mid Stent

Figure 7A:
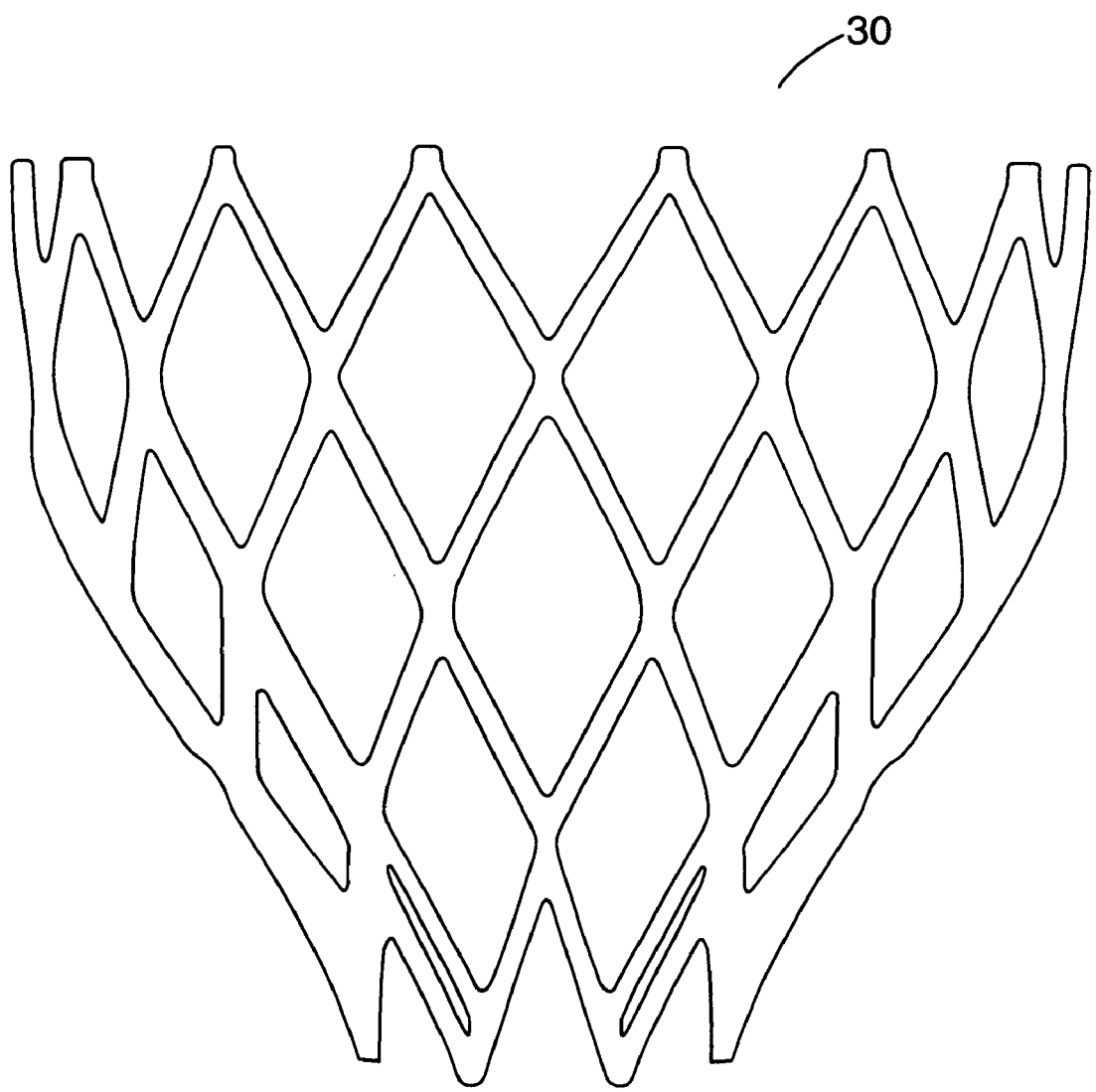
FIG. 7A shows a side view of the mid-stent of the present invention and FIG. 7B shows a top view of the mid-stent.
Figure 7B:
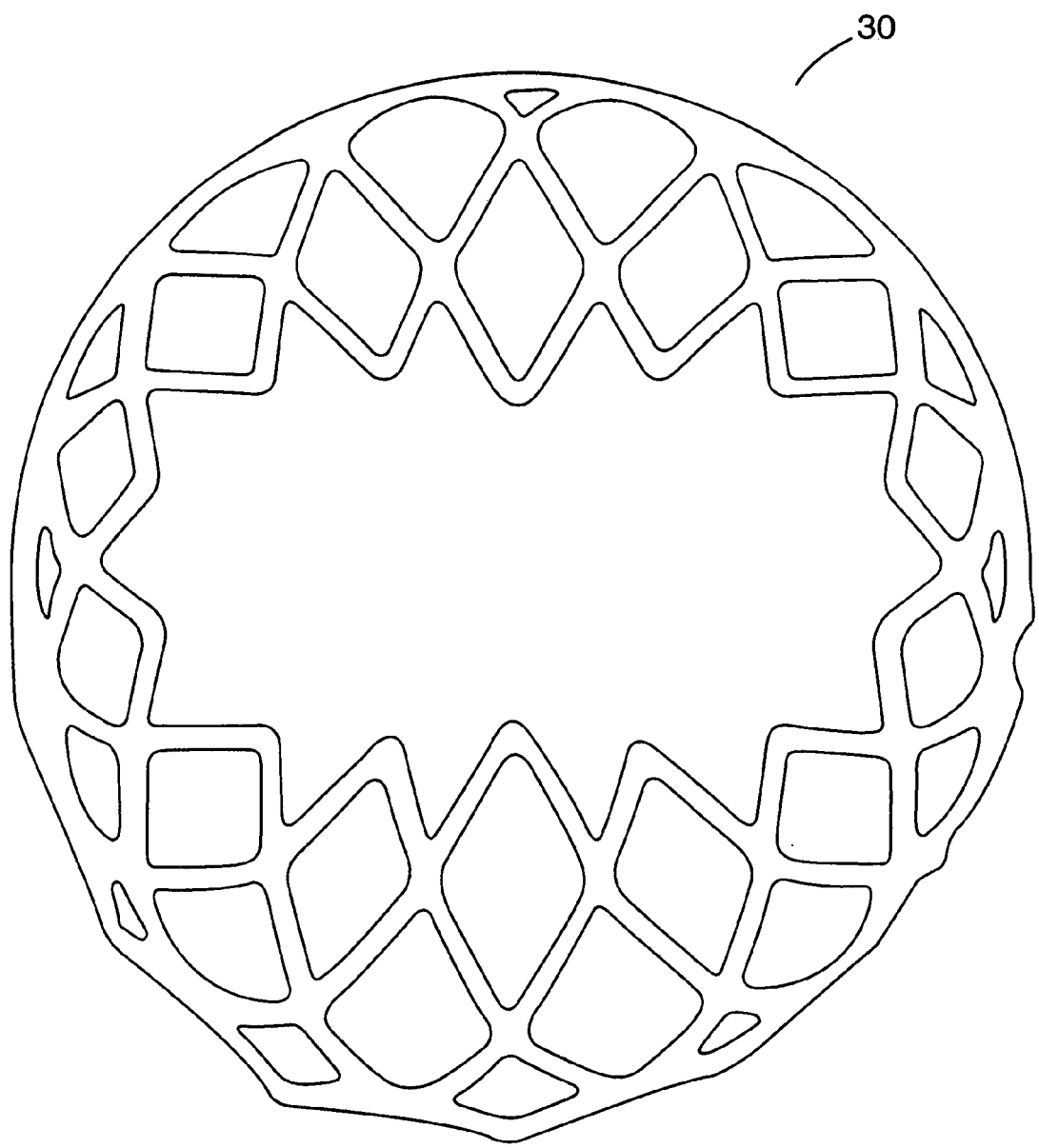

Mid-stent 30 is attached to the inside of the graft (trunk 12) just below the caudal end of aortic stent 10. Mid-stent 30 provides support and structure to trunk 12 where the graft transitions from a single lumen to branches 14 and 16. It preferably is formed from a laser cut tube and shape set into a diamond like mesh pattern, as shown in FIGS. 7A and 7B. FIG. 7A shows a side view of the mid-stent, shaped so that the upper (or cranial) diameter matches that of the aortic stent. FIG. 7B shows a top view of the mid-stent and shows that the caudal portion of the stent is shaped to join branches 14 and 16. The dimensions of a mid-stent, for example, is approximately 30 mm in length, comprising a diamond like mesh having struts that are approximately 7.5 mm long, with 14 circumferentially oriented zigzags. The mid-stent is preferably cut from an initial tube of 0.267 cm ID by 0.356 cm OD (0.105 in. ID by 0.140 in. OD).

The mid stent is shape set on a mandrel with a tapering shape, inducing the tapering contour to the stent. This contour helps create a smooth transition to the graft structure from a single lumen (trunk 12) to two lumens (branches 14 and 16). Thus, the caudal portion has a smaller diameter, or opening, than the cranial portion. Further, the caudal portion may be formed so that the opening approaches a figure eight shape.

Since at least a portion of the mid-stent is constrained by the non-aneurysmal portion of the aorta, this stent too is subjected to the same pulsatile motion as the aorta and aortic stent. Therefore, the struts are processed in a manner similar to those in the aortic stent. The intersecting regions of struts have the same shape as those for the aortic stent, and the struts have a reverse taper, (wider at the middle of the strut than near the intersections) similar to the cranial struts of the aortic stent above.

Iliac Stents

Figure 8:
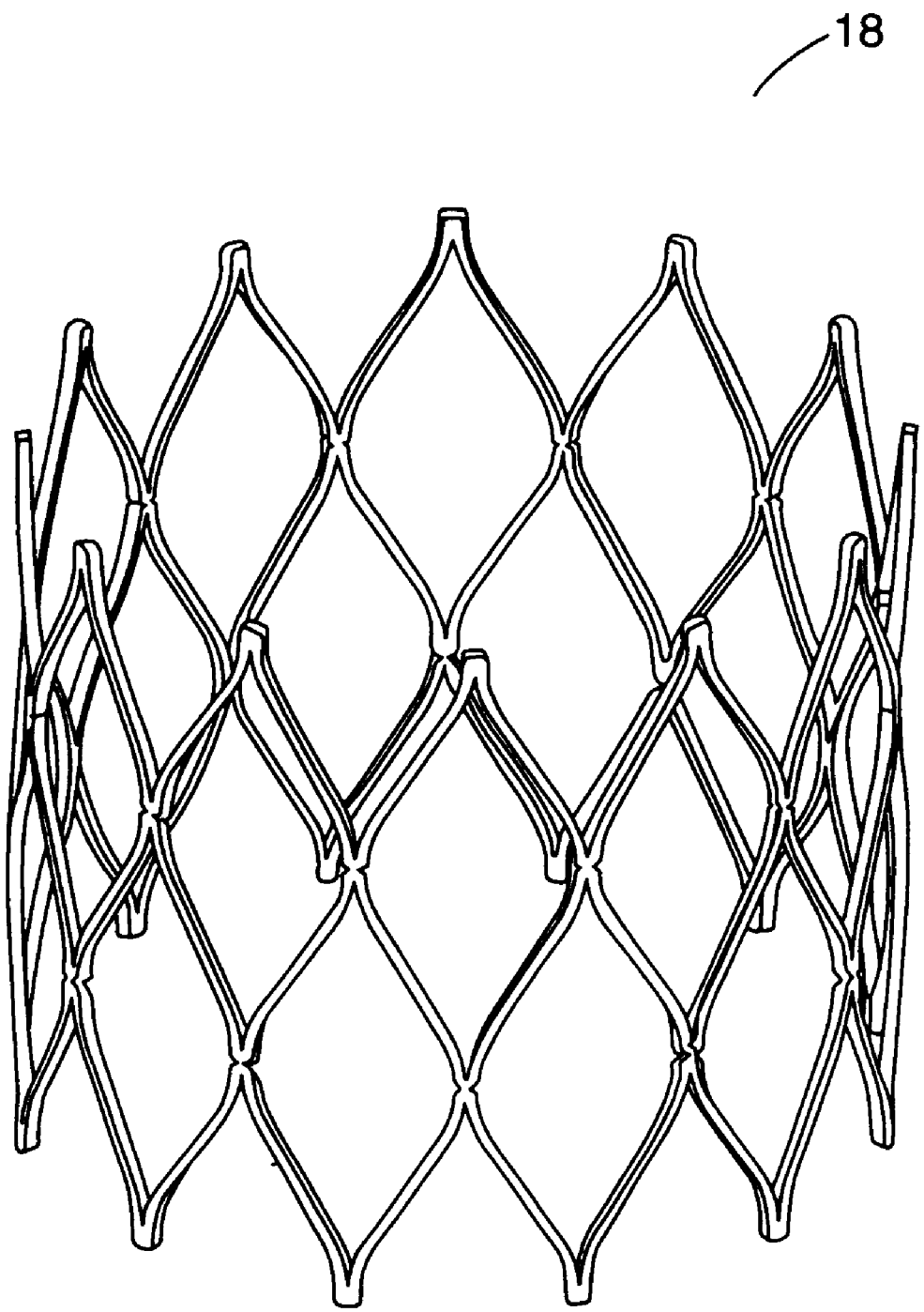
FIG. 8 is a perspective view of the iliac stent of the present invention.

FIG. 8 illustrates iliac stent 18 having a series of zigzag struts connected together. Iliac stent 18 preferably is formed of three connected zigzags. The junction of the struts is similar to those discussed in connection with the cranial struts of aortic stent 10 shown in FIGS. 6B and 6C.

Iliac stents preferably are fabricated from a laser cut tube of initial dimension 0.229 cm ID by 0.318 OD (0.090 in. ID by 0.125 in. OD). Like both the aortic stent, and the mid-stent, the struts are processed to minimize strain near the strut intersections. The struts and intersections are similar in design to those in the mid-stent and aortic stent. As in the aorta, the iliac arteries exhibit pulsatile wall motion, and since the iliac stents would be constrained by the iliac arteries, they will be cyclically stressed, and would therefore benefit from lower stress. The struts are preferably 0.0229 cm (0.009 in.) wide adjacent the four strut intersections, and 6 mm long, having a reverse tapering strut width similar to that of the aortic stent.

Also, to minimize the number of different diameter combinations of graft systems, it is preferred that the iliac stent have an expanded diameter of 16 mm. when expanded. Similarly, the proximal portion of the graft material forming the legs is flared, having a diameter of 16 mm. This single diameter for the iliac ends of the graft system would enable its use in iliac arteries having a non-aneurysmal region of a diameter from preferably between 8 and 14 mm in diameter. It is also contemplated that multiple diameter combinations of iliac stent and graft flare would be desirable.

Support Stents

Figure 9:
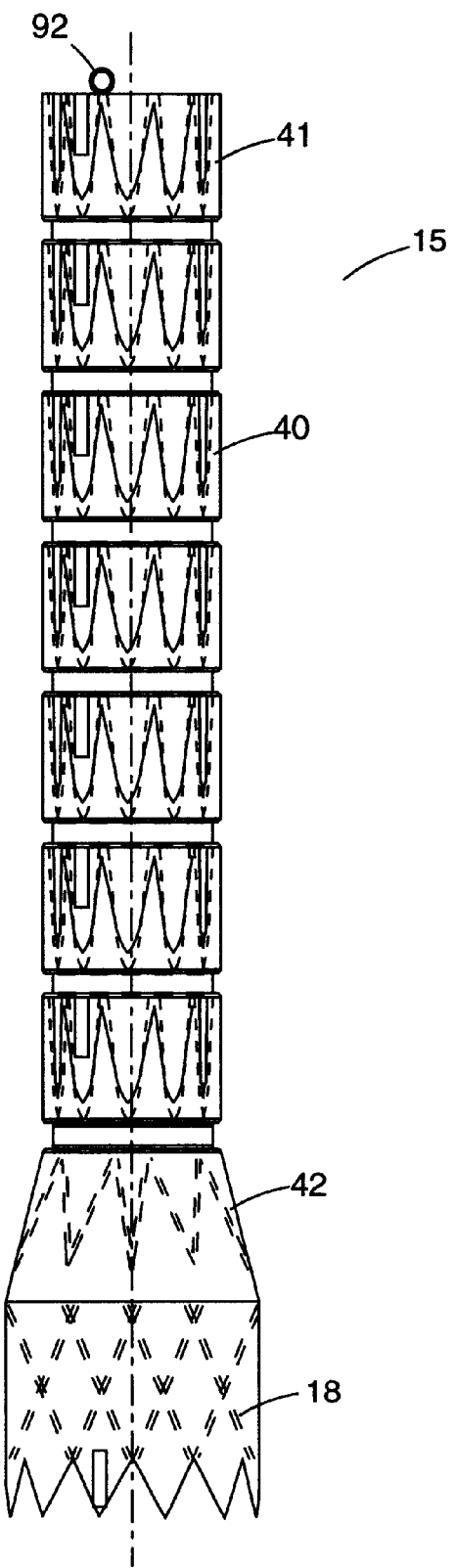
FIG. 9 is a perspective view of one leg of the graft system of FIG. 3A.

FIG. 9 illustrates one leg of the endovascular graft system, showing iliac stent 18 at the caudal end, and support stents 40, 41, and 42. In order to illustrate the relationship of these various parts the leg in FIG. 9 is shown as though the graft material were transparent. The stents are formed from a shape set laser cut tube, similar to the stents described above. Support stents are preferably formed to 11 mm in diameter, and are a single circumferential row of zigzags, preferably 10 zigzags. These stents are formed with uniform width connections at the intersections of the struts, as in the above stent structures. These stents are preferably cut from tubing of 0.251 cm ID by 0.317 cm OD (0.099 in. ID by 0.125 in. OD). The strut widths are preferably about 0.33 cm (0.013 in.) wide adjacent the two-strut intersections. The struts are preferably about 7 mm long.

Lower most support stent 42 has a tapered profile, having a diameter at one end the same as support stents 40, and a diameter at the other end matching the diameter of iliac stent 18.

Figure 10:
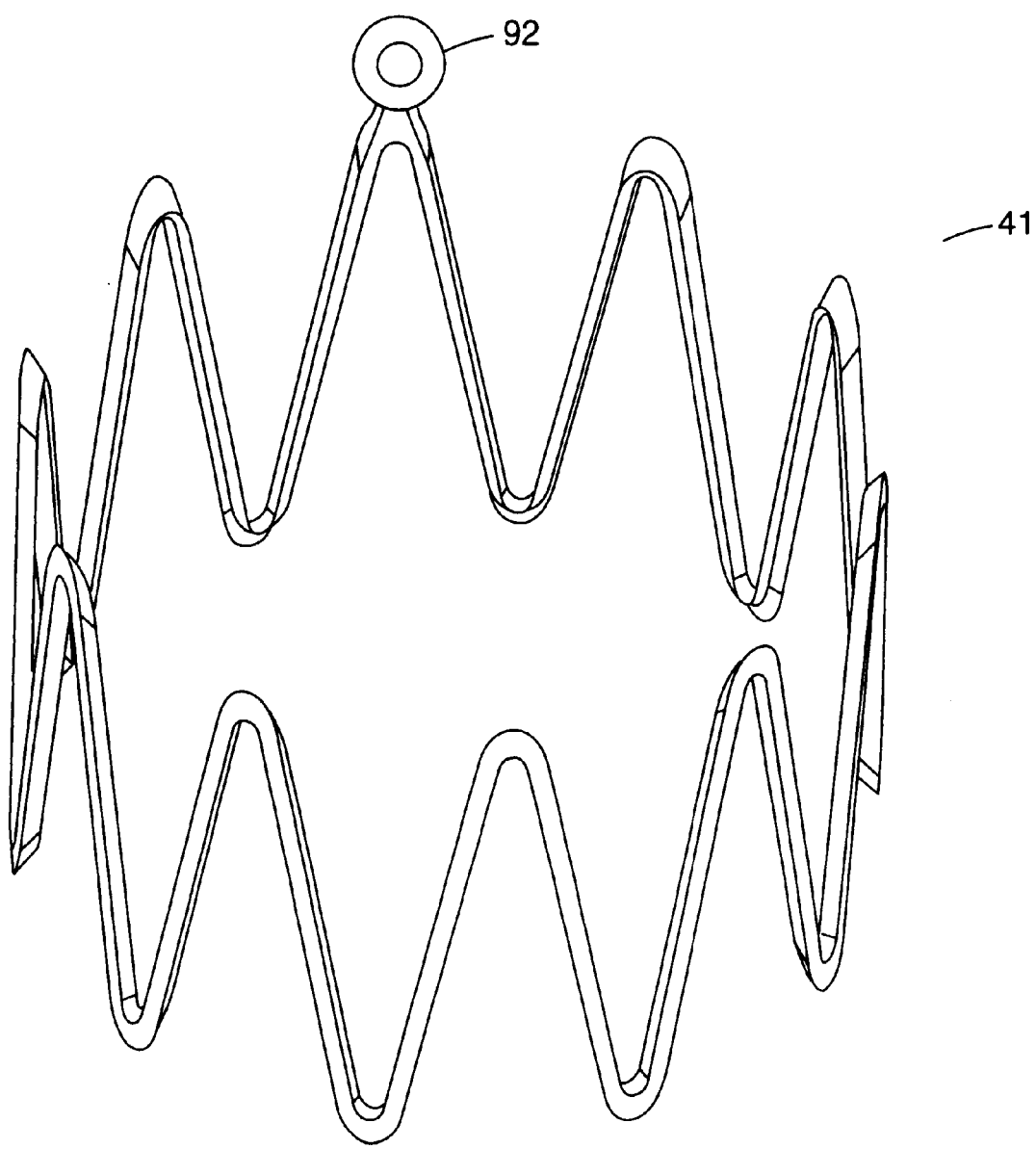
FIG. 10 is a perspective view of a support stent of the present invention.

Upper most support stent 41 for the ipsilateral leg, as shown in detail in FIG. 10, differs from support stents 40 in that it has eyelet 92 on one of the upper strut connections. This eyelet is used to stabilize the position of the leg during deployment as will be described in more detail in the delivery catheter section. The contralateral leg has a similar eyelet.

Stent Materials and Processing

Support stents 40, iliac stents 18 and 19, mid stent 30, as well as aortic stent 10, preferably are self-expandable and typically are comprised of a shape memory alloy. Such an alloy can be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising 55.8% Ni by weight, commercially available under the trade designation NITINOL. This NiTi alloy undergoes a phase transformation at physiological temperatures. A stent made of this material is deformable when chilled. Thus, at low temperatures (e.g., below 20° C.), the stent is compressed so it can be delivered to the desired location. The stent is kept at low temperatures by circulating chilled saline solution. The stent expands when the chilled saline is removed and it is exposed to higher temperatures within the patient's body, e.g., 37° C.

Preferably, each stent is fabricated from a single piece of alloy tubing. The tubing is laser cut, shape-set by placing the tubing on a mandrel, and heat-set to its desired expanded shape and size.

Preferably, the shape setting is performed in stages at 500° C. That is, the stents are placed on sequentially larger mandrels and briefly exposed to 500° C. For most of the stents, at least two increasingly larger mandrels are required to set the final size without unduly stressing the stent. To minimize grain growth, the total time of exposure to 500° C. is limited to 5 minutes. The stents are then given their final shape set for 4 minutes at 550° C., and then "aged" at 470° C. (to impart the proper martensite to austenite transformation temperature), then blasted (as described below) before electropolishing. This heat treatment process provides for a stent that has a martensite to austenite transformation which occurs over a relatively narrow temperature range (e.g. 15 centigrade degrees).

To improve the mechanical integrity of the stent, the rough edges left by the laser cutting are removed by a combination of mechanical gritblasting and electropolishing. The grit blasting is performed to remove the brittle "recast" layer left by the laser cutting process. This layer is not readily removable by the electropolishing process, and left intact, could lead to brittle fracture of the stent struts. A solution of 70% methanol and 30% nitric acid at a temperature of −40° C. or less has been shown to work effectively as an electropolishing solution. Electrical parameters of the electropolishing are selected to remove approximately 0.00127 cm (0.0005 in.) of material from the surfaces of the struts. The clean, electropolished surface is the "final" desired surface for attachment to the graft materials. This surface has been found to impart good corrosion resistance, fatigue resistance, and wear resistance.

Graft Material Components

Graft material 45 of trunk 12, branches 14 and 16, and legs 15 and 17 may be made of materials which include woven, knitted, sintered, extruded, or cast materials comprising polyester, polytetrafluoroethylene (PTFE), silicones, urethanes, and ultralight-weight polyethylene, such as that commercially available under the trade designation SPECTRA™. The materials may be porous or nonporous. Preferred material includes a woven polyester fabric made from DACRON™ or other suitable PET-type polymer.

A preferred fabric for the graft material is a 40 denier 27 filament polyester yarn, having about 70 to 100 end yarns per cm per face (180 to 250 end yarns per inch per face) and 32 to 46 pick yarns per cm per face (80 to 120 pick yarns per inch per face). At this weave density, the graft material is relatively impermeable to blood flow through the wall, but yet is relatively thin, ranging between 0.08 and 0.12 mm wall thickness.

The graft material for trunk 12 is preferably woven as a seamless bifurcating weave, woven flat on a standard Dobby loom. Preferably a taper is incorporated between the single lumen upper portion of the woven graft trunk and the two smaller diameter lumens. To enable this taper, the pick (weft) yarns are interwoven around every two warp yarns. This allows for a tight relatively impermeable weave for the upper portion of the trunk, and the ability to "pack" the weave even more densely for the tapering portion and the two branches.

The graft material of legs 15 and 17 preferably are woven of the same material as trunk 12. These graft components are single lumen tubes, and preferably have a taper and flared portion woven directly from the loom, as illustrated for leg 15 in FIG. 9.

Prior to attachment of the stents, crimps are formed in the trunk and leg graft components between the stent positions by placing the graft on a shaped mandrel and thermally forming indentations in the surface. Preferably, crimps 41 (as shown in FIGS. 4 and 5) in the graft are about 2 mm long and 0.5 mm deep. With these dimensions, the graft system, with the support stents 40 attached, can bend and flex, yet maintain an open lumen.

Also prior to attachment of aortic stent 10 to trunk 12, the graft material of trunk 12 is cut in a shape to mate with the aortic stent (i.e., in a zigzag pattern). Preferably, the caudal ends of the leg grafts are also shaped to match the iliac stent.

Attachment of Stent Components and Graft Components

Each stent (i.e., aortic stent, mid-stent, iliac stent, and support stents), is attached to the appropriate graft component with suture material. The suture material is preferably polyester braided 5/0 surgical suture impregnated with PTFE (polytetrafluoroethylene) strands. A preferred suture material is Silky II Polydeck™ by Genzyme.

The method of suturing stents in place is important for minimizing the relative motion or rubbing between the stent struts and the graft material. Because of the pulsatile motion of the vasculature and therefore the graft system, it is possible for relative motion to take place, particularly in areas where the graft system is in a bend, or if there are residual folds in the graft material, due to being constrained by the aorta or iliac arteries.

Ideally, each strut of each stent is secured to graft material by suture thread. A preferred type of stitch is a "blanket stitch", which serves to securely holds the struts at numerous points against the graft material. A secure hold is desirable in preventing relative motion in an environment in which the graft system experiences dynamic motion arising from pulsatile blood pressure, in addition to pulsation of the arteries that are in direct mechanical contact with the graft system. The struts nearest the aortic and iliac ends of the graft system are subject to the pulsatile motion arising from arterial contact. These struts in particular should be well secured to the graft components. It is difficult to manipulate the suture thread precisely around struts that are inside the graft component (i.e., some distance away from an open end), so various stitches, or none at all, may be used there.

As shown in FIG. 3, the lower struts in the aortic stent are secured to the cranial end of the graft material of trunk 12, which has been cut to match the shape of the stent. The blanket stitching completely encircles the strut and "bites" into the graft material. Preferably, the stitch encircles the strut at approximately five equally spaced locations. The struts are positioned on the outside of the graft material for this particular attachment, however, the struts could be positioned on the inside surface as well.

The mid-stent also is secured to the aortic graft component with the use of blanket stitching. The upper and lower zigzag patterns of struts on each end of the mid-stent are secured in this fashion. Individual point stitches are used to secure the middle strut intersections to the inside surface of the graft component.

For the attachment of the support stents into the trunk graft material, as well as each of the leg graft components, the ends of the stents are secured via individual point stitches at several positions such as 37, as shown in FIG. 3B.

Once the graft system is fully implanted into the aneurysm, the aortic and iliac ends of the graft system will be in direct contact with the blood vessel, and therefore subject to the pulsatile motion of those blood vessels. However, a significant length portion of the implanted graft system will not rest directly against vascular tissue. This portion of the graft system will be within the dilated aneurysm itself. Therefore, this portion of the graft system will not experience any significant pulsatile motion. For this reason, it is not necessary to secure these stents to the graft material as aggressively as the stent structures described above. Therefore only point stitches are necessary for securing the support stents.

Although not shown in the figures, iliac stents are secured to the graft material by means of sutures, preferably blanket stitching, at the upper and lower zigzags.

Graft Delivery System

In the preferred embodiment of the graft system, two separate delivery catheters are utilized to deliver the three graft structures. The first delivery catheter 110, as shown in FIGS. 12–18 is used to deliver the aortic trunk and a first leg. This delivery system is referred to as the "ipsilateral" delivery system. A second delivery catheter ("contralateral" delivery system) is used to deliver the second leg graft into the second branch of the aortic trunk, and is delivered from the opposite femoral artery as the first delivery system.

Figure 12:
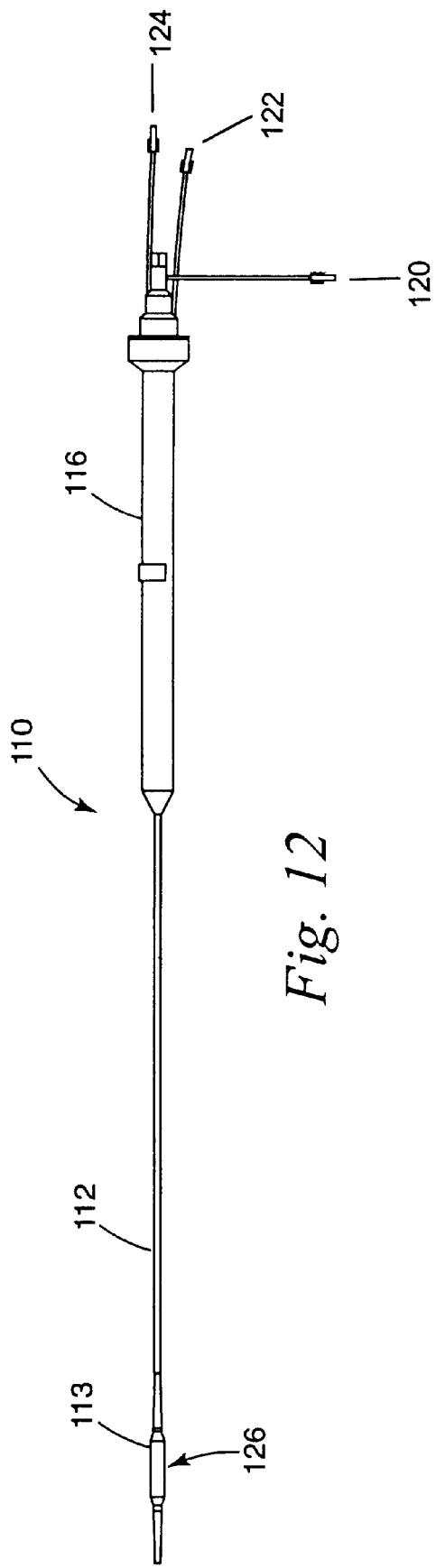
FIG. 12 illustrates a view of the delivery system used to insert and deploy a portion of the graft system of the embodiment of FIG. 3.
Figure 13:
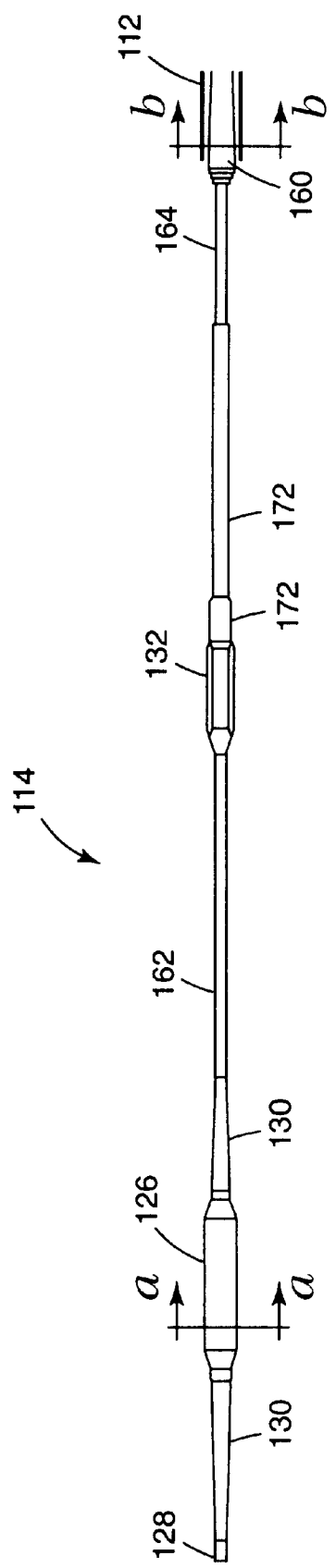
FIG. 13 is a view of the delivery system of FIG. 12 with the outer sheath retracted.
Figure 14:
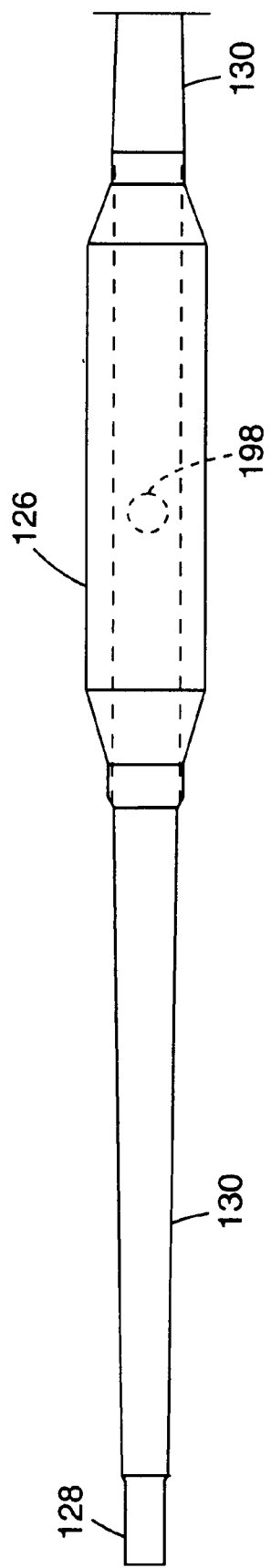
FIG. 14 illustrates an enlarged view of a distal portion of the delivery system of FIG. 12.

FIG. 12 is a view of the delivery catheter 110 including outer sheath 112 and handle 116. FIG. 13 is a view of the distal portion of the same catheter with the outer sheath 112 fully retracted to expose inner catheter 114. Outer sheath 112 and inner catheter1 14 are connected to handle 116. Handle 116 at the proximal end of the delivery system causes relative sliding motion between sheath 112 and inner catheter 114 to facilitate delivery of the graft structures as will be described more fully hereafter with respect to FIG. 16. The graft structures (which are not shown in FIGS. 12–18) are positioned in a folded and compressed state in an annular space between outer sheath 112 and inner catheter 114, toward the distal end of the delivery system.

The handle contains three fluid delivery ports 120, 122, and 124 as shown in FIG. 12. First port 120 communicates with balloon structure 126 near the distal end of the inner catheter, second port 122 communicates with the lumens 123 defined by a saline delivery tube 160 (FIG. 15B), for delivery of chilled saline, and third port 124 communicates with an outlet 125 (FIG. 18) on the inner catheter for delivery of radiopaque contrast media. These fluid delivery paths will be discussed in more detail below.

Referring to FIG. 12, outer sheath 112 is positioned with its distal tip 113 overlapping an inflated balloon 126. The inflated balloon provides for a smooth tapering transition for the outer sheath. This will be described in more detail below. In this configuration, with the graft structures loaded in a folded and compressed state, the catheter is introduced into the patient's vascular system for delivery of the graft structures.

Inner Catheter

Inner catheter 114 and handle 116 are shown in FIGS. 12 and 13. Near the distal end is a composite balloon tip structure. The inflatable balloon 126 is inflated during introduction of the delivery catheter into the vasculature and to the desired delivery site within the aneurysm. The balloon is attached to a balloon catheter shaft 128. This balloon catheter shaft runs the entire length of the delivery catheter and attaches to the handle mechanism near the proximal end. The proximal end of the handle mechanism is non-moving/non-rotating. The balloon catheter shaft has a lumen 194 the entire length for passage of a conventional 0.089 to 0.96 cm (0.035 or 0.038 in.) diameter guidewire. An additional pathway 196 in the balloon catheter shaft carries inflation media to the balloon for inflation and deflation through port 198. The inflated balloon is preferably slightly larger in OD, than the sheath ID, to assure a smooth tight fit. The inflated balloon prevents the leading edge of the outer sheath from "catching" or "snagging" on the walls of the vasculature. The balloon tapers at both ends, and is preferably fabricated of a relatively non-compliant polymer such as nylon. The balloon is preferably about 3 cm in length.

Figure 15A:
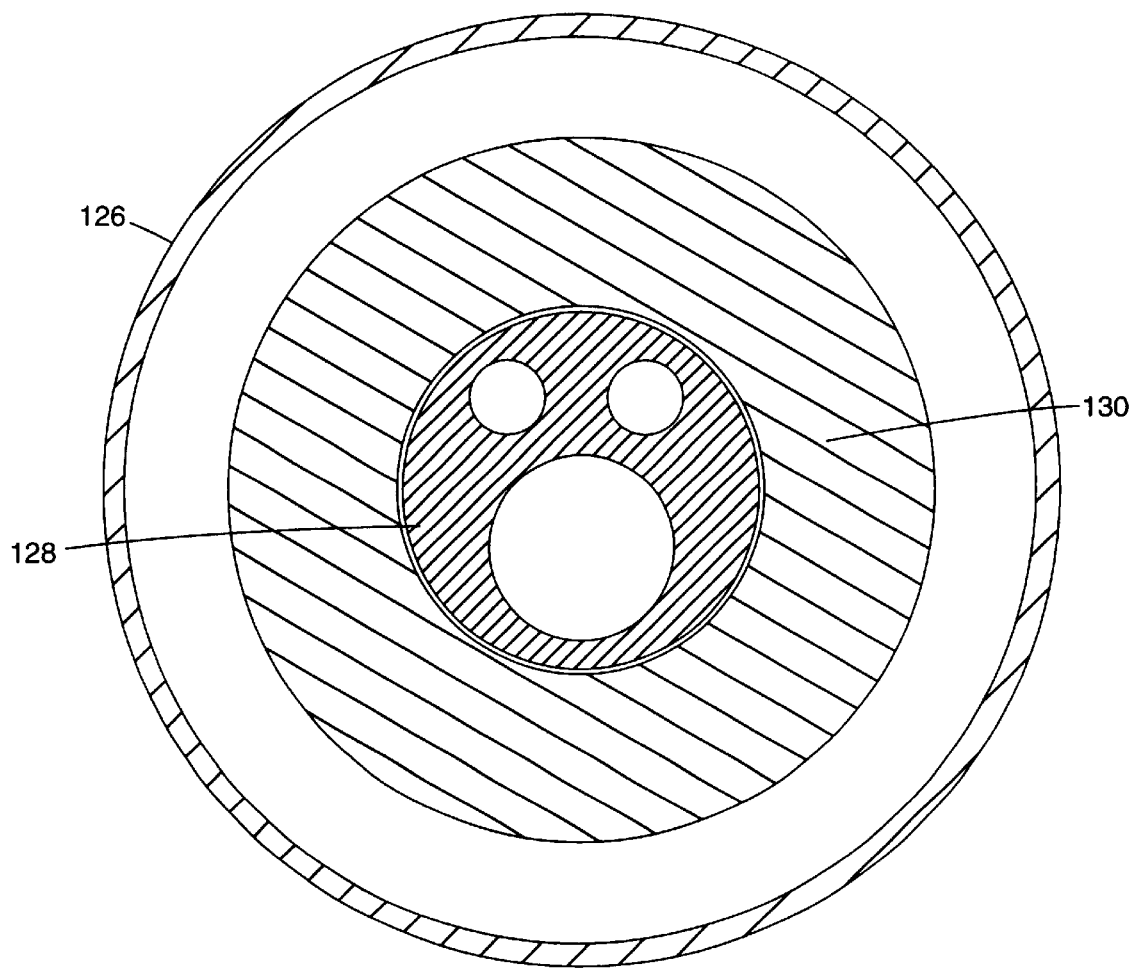
FIGS. 15A and 15B are cross-sectional views taken along lines a—a and b—b of FIG. 13, respectively.

On the outside of the balloon catheter shaft is a distal tapering transition 130, hereafter referred to as DTT. The DTT preferably is fabricated from an elasomeric copolymer commercially available under the trade designation PEBAX from Elf Atochem. The DTT provides a transition in flexibility from the distal-most portion of the inner catheter, to and through the balloon structure. When the delivery system is being advanced into and through tortuous vasculature, the DTT helps guide and flex the relatively stiffer outer sheath over the more flexible guidewire and around bends in the vasculature. Without this structure, there would be an abrupt transition in stiffness between the guidewire and the stiffer sheath, and trackability through curves would be greatly inhibited. FIG. 15A is a cross-sectional view of the inner catheter along line a—a through the middle portion of the balloon. Balloon 126, DTT 130, and balloon catheter shaft 128 can be seen.

Proximal to balloon 126, DTT 130 tapers inwardly to a smaller dimension. The aortic stent is disposed about this region of the transition element when loaded in the delivery catheter. To minimize the chance of kinking during advancement and tracking of the delivery system, it is desirable to maintain a relatively uniform lateral stiffness along the length of the loaded delivery catheter, with only smooth, gradual changes in stiffness. Without the proximal portion of the transition element in place, the delivery system could have a weak, kink prone region just proximal to the inflated balloon, and therefore the presence of the transition element helps prevent kinling of the sheath.

Further proximal to the tapering transition element, the balloon catheter shaft is supported by a distal reinforcing tube 162, preferably of polyimide having a wall thickness of about 0.0035 inches (0.0014 cm) and an outer diameter of about 0.09 inches (0.035 cm). It is in this region where the bifurcated upper graft trunk resides when the delivery catheter is loaded. When loaded in the delivery catheter, the folded and compressed graft material in this region adds stiffness when compared to the region with the aortic stent. Therefore, a lower stiffness is required for the inner catheter in this region than in the region closer to the balloon 126. The inner catheter in this region comprises balloon catheter shaft 128, and thin walled tube 162, attached to the outside of the balloon catheter shaft.

Figure 18:
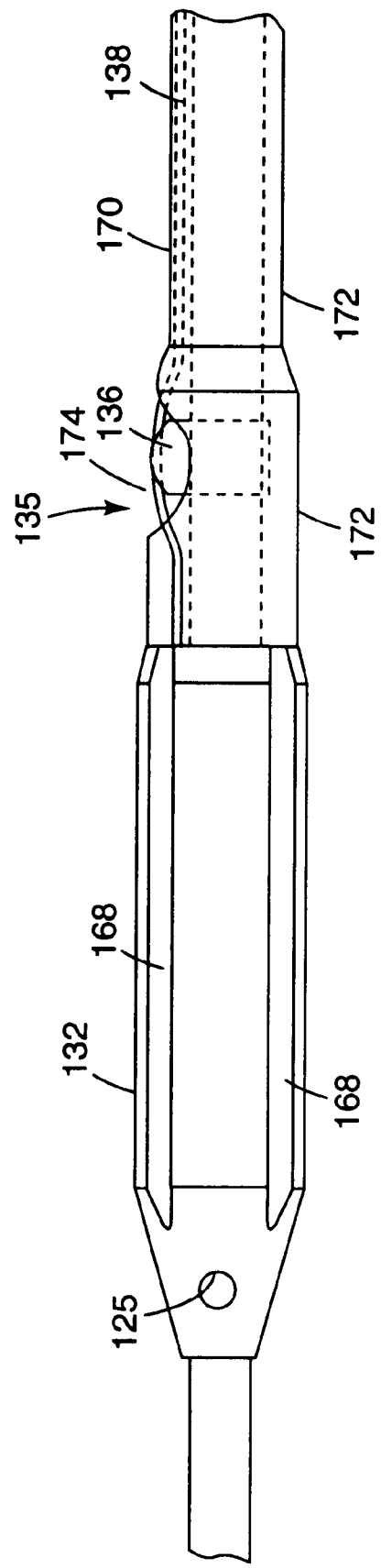
FIG. 18 is a partial view of the proximal tapering transition element and wire stabilizer of the catheter of FIG. 12.

Proximal to the folded and compressed aortic trunk (attached to the aortic stent) in the delivery system is proximal tapering transition element 132, hereafter referred to as PTT. The distal end of PTT 132 is fixed about the outside of the balloon catheter shaft as can be seen in FIG. 18 which is an enlarged view of a portion of the inner catheter including the PTT and the stabilizing mechanism. The distal end of PTT 132 has a tapering diameter from the OD of the balloon catheter shaft to a diameter approximately equal to the ID of the distal end of the outer sheath. Following delivery of the aortic trunk component, the distal end of the outer sheath rests on the maximum diameter region of PTT 132. The entire delivery catheter is then advanced into the aortic trunk until the desired position for delivery of the ipsilateral leg component is reached. The tapering diameter of the distal end of PTT 132 facilitates the advancement of the delivery catheter, minimizing any "snagging" or "catching" of the distal tip of the outer sheath on the inside of the aortic trunk graft material.

On the major diameter portion of PTT 132 is series of longitudinal grooves 168. These grooves provide an outlet for the chilled saline that is infused on the inside of the outer sheath during delivery, to keep the shape memory stent components in a compressed state.

Proximal to the PTT is a stabilizing mechanism 135 for securely holding the distal position of the ipsilateral leg during delivery. It is important for the ipsilateral leg to be maintained longitudinally taut while the outer sheath is being withdrawn. This is accomplished by means of a stabilizing wire, which keeps the upper-most stent in the ipsilateral leg graft from migrating proximally in the delivery catheter during sheath retraction. If this stent is not prevented from migrating, and it does migrate during sheath retraction, the leg will compact longitudinally in the delivery system, and once it is fully exposed and expanded, the blood pressure inside the graft will re-lengthen it, and the combined aortic trunk and leg will be longer than desired. The extra length will cause the ipsilateral leg graft to "bow" or "snake" inside the aorta and iliac arteries, which is undesirable.

The stabilizing mechanism consists of clip 136 and stabilizing wire 138 that runs through clip 136. The upper-most stent of the leg graft has an eyelet attached to one of the struts, as shown in FIG. 9B. attached to one of the struts. When loaded in the delivery catheter, the stabilizing wire passes through the eyelet. The stabilizing wire runs in lumen 170, as shown in FIG. 18. This lumen is defined by a protector sheath 172 which surrounds the stabilizing mechanism, and has an opening 174 for the clip and a portion of the stabilizing wire. Just distal of the clip is where the eyelet of the upper stent is positioned. The eyelet and stent are then securely positioned between the clip and the lumen which contains the stabilizing wire farther proximally.

Once the delivery catheter is positioned in the proper position within the aneurysm, the outer sheath is retracted relative to the inner catheter, and the folded compressed graft segments. The aortic trunk is exposed, and expands into position in the aneurysm. The delivery catheter is then advanced into this trunk until the lower end of the ipsilateral leg component is in proper position, relative to the internal iliac artery. This assessment is aided by introducing contrast fluid into the vasculature via the contrast delivery port. Once positioned, the outer sheath is then withdrawn further via manipulation of the delivery handle. As the ipsilateral leg is exposed, the upper end begins to expand within the branch of the aortic trunk graft. The stabilizing wire is still engaged into the eyelet of the upper support stent.

Figure 16:
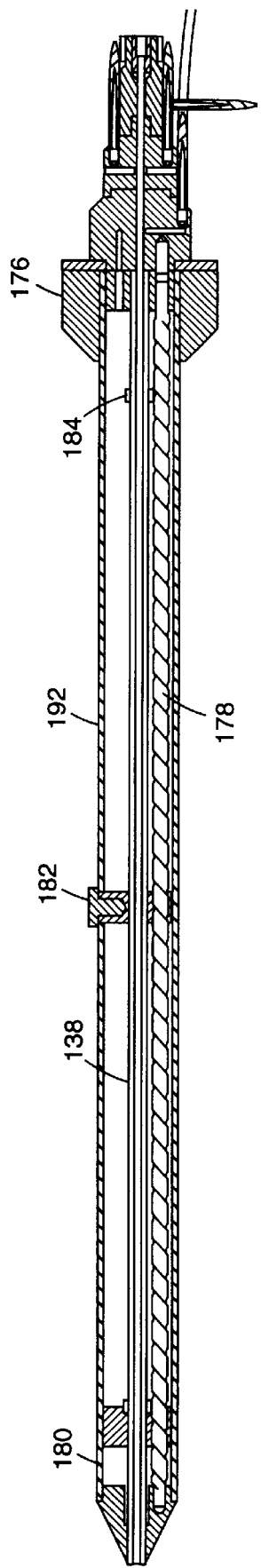
FIG. 16 is a cross-section view of the handle of the delivery catheter of FIG. 12.

As best seen in FIG. 16, the outer sheath is retracted by manipulating a rotating knob 176 which rotates threaded rod 178. Outer sheath 112 is connected to outer sheath mount mechanism 180. Rotation of knob 176 causes threaded rod 178 to move outer sheath mount mechanism 180 proximally. When mechanism 180 reaches pin 182 the aortic trunk graft component has been deployed. Pin 182 is then removed to allow deployment of the ipsilateral leg component of the graft system once advanced within the trunk to the proper location. Once the sheath is withdrawn to the location of the iliac stent, mechanism 180 engages actuator 184 and begins to move it proximally, together with the outer sheath. Actuator 184 is connected to stabilizing wire 138 which is also caused to be withdrawn. The stabilizing wire is threaded through the eyelet at a location just distal of the clip. As the stabilizing wire is withdrawn it is retracted through the eyelet. The stabilizing wire is fully disengaged from the eyelet just prior to full exposure and expansion of the iliac stent. The delivery catheter can now be removed from the ipsilateral vasculature.

Referring again to FIG. 13 and FIG. 15B, proximal to the stabilizing mechanism on the inner catheter, the inner catheter shaft contains proximal support tube 164. This tubing defines the contrast lumen 166, which leads into the PTT and out the port 125. This tubing component is placed coaxially surrounding the polyimide stiffening tubing 162 already described, and extends proximally. While defining the contrast lumen, this tubing also adds additional stiffness to the inner catheter, over and above the stiffness provided by the balloon catheter shaft and the polyimide shaft. This additional stiffness "makes up" for the lower stiffness of the compressed and folded ipsilateral leg component, such that the stiffness of the delivery system is maintained relatively the same as the stiffness distally. Preferably this tubing component is comprised of a rigid material, such as polyetheretherketone (PEEK), or polyimide.

Figure 15B:
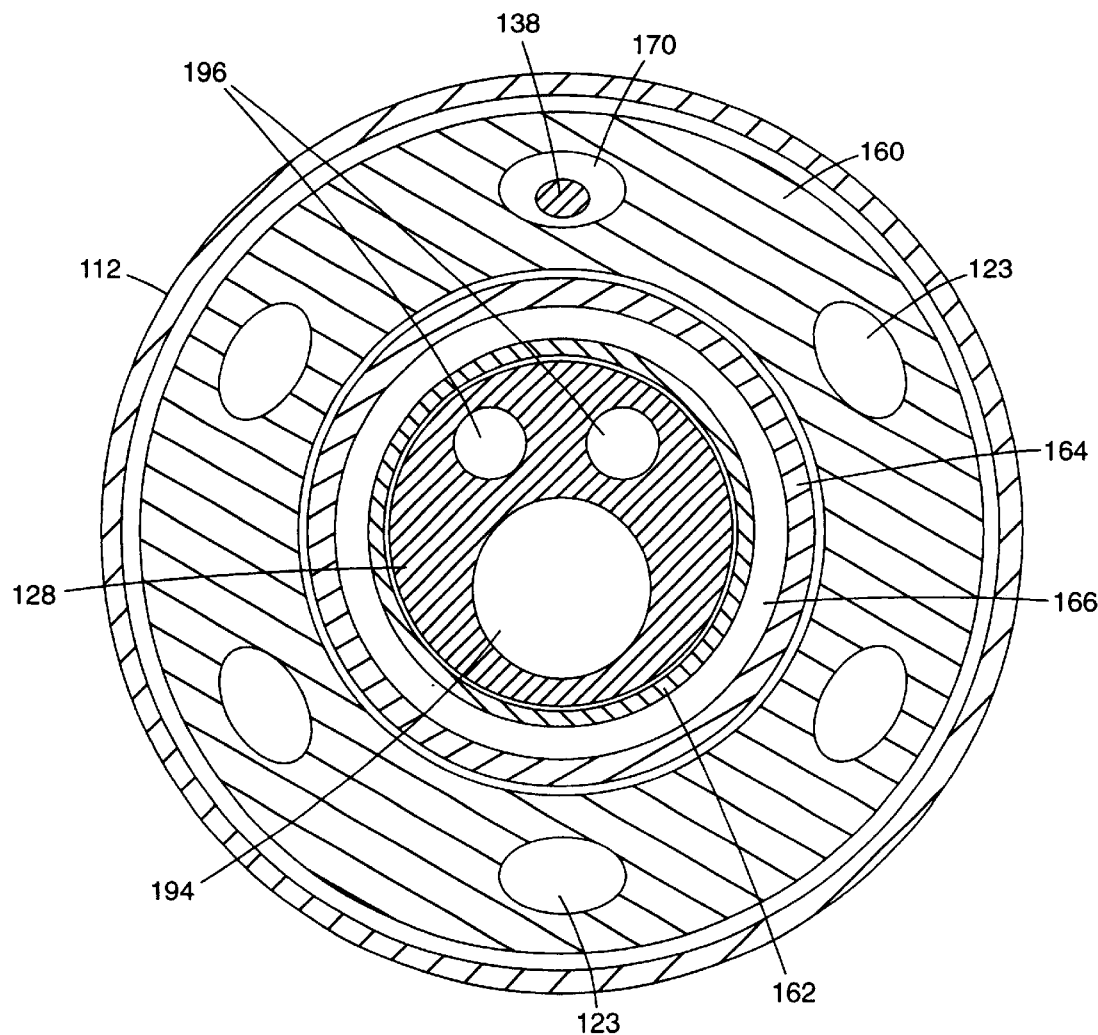

Proximal to the region holding the ipsilateral leg is the proximal shaft region of the inner catheter, shown in FIG. 15B. The inner catheter in this region has an additional component, the saline delivery tube. FIG. 15B is a cross section showing the construction of the delivery catheter in this region. The saline delivery tube is coaxially positioned about the other tubular structures of the inner catheter, and contains a central lumen, inside of which are tubes 162, 164, and the balloon catheter shaft 128. The contrast lumen 166 described above is defined by the space between the proximal support tube 164 and the distal support tube 162. There are preferably six lumens within the wall of the saline delivery tube, five of which are used to deliver chilled saline into the outer sheath, and over the folded compressed graft components when loaded into the delivery catheter. The stabilizing wire 138 resides in the other lumen 170, and extends proximally into the delivery handle mechanism. The saline delivery lumens 123 exit into the annular space between the inner catheter and the outer sheath at the distal end of the saline delivery tube.

The saline delivery tube is preferably constructed of polyethylene, and is sized to fit closely to the inner diameter of the main sheath. In this fashion, the saline delivery tube adds stiffness to the completed delivery catheter, and the size prevents potential kinking of the outer sheath in this region of the catheter.

The distal and proximal support tubes 162 and 164 indicated in FIG. 15B extend only a few cm proximal of the distal end of the saline delivery tube. The proximal support tube is adhesively bonded to the inner surface of the central lumen of the saline delivery tube, and the polyimide tube is adhesively bonded to the outer surface of the balloon catheter shaft. The proximal shaft of the balloon catheter is connected to the delivery handle in a fashion which fixes its position with respect to the outside of the delivery handle.

Outer Sheath

Figure 17:
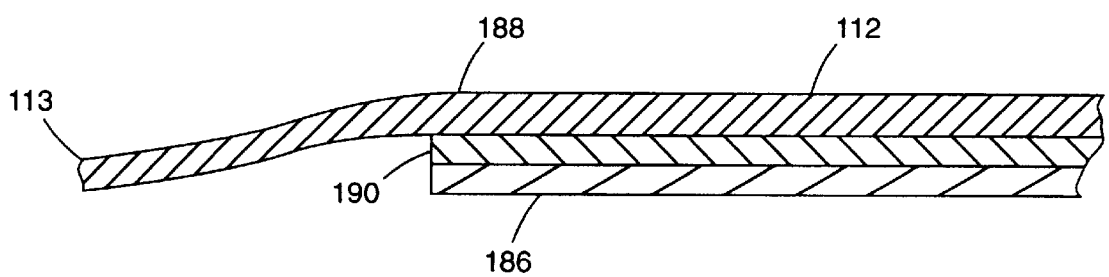
FIG. 17 is a partial enlarged view of the distal end of the outer sheath of the delivery catheter of FIG. 12.
Figure 17:
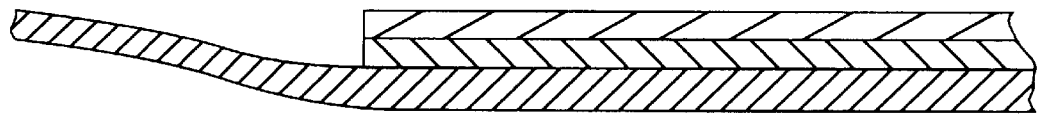

The outer sheath preferably has three different layers, as shown in FIG. 17, which is a view of the distal tip of the outer sheath. The inner lining 186 of the sheath is preferably polytetrafluoroethylene (PTFE), to minimize friction of the sheath as it retracts from the folded and compressed graft components. The outer layer 188 is preferably cross-linked heat-shrinkable polypropylene, to minimize friction of the outside against the vasculature, and provide high longitudinal rigidity (to prevent stretching during sheath retraction). An intermediate layer 190 is low density polyethylene, which when heated to near its melting temperature, fuses the polypropylene to the PTFE. The PTFE has an etched exterior surface to facilitate adhesion of the LDPE to the polypropylene.

At the distal tip, as shown in FIG. 17, the outer or polypropylene tube 188 is projected and beveled down beyond the PTFE and middle layers. This allows for the very tip to present a very thin "profile" atop the inflated balloon of the inner catheter. This helps to minimize the chance of the tip snagging during advancement of the delivery system in the vasculature. Additionally, after the outer sheath has been withdrawn to the proximal transition element 132, the leading edge again presents a very low profile, minimizing the chances of snagging.

In a preferred embodiment, the sheath is sized to the graft size, and could be, for instance, approximately 0.599 cm (0.236 in.) ID by 0.676 cm (0.266 in.) OD. The projecting tip is beveled inward to an ID of approximately the same 0.599 cm (0.236 in.).

Alternative materials for the sheath and tip construction are also contemplated. For example, an elastomeric material could be used for the outer layer of the sheath, or for just a distal portion of the outer layer of the sheath, and could be formed to a smaller inner diameter, for example 0.584 cm (0.230 in.) In this fashion, the tip would fit snugly against the PTT when the sheath is withdrawn, further lowering the profile of the sheath tip, and further minimizing snagging or hanging up during subsequent advancement of the delivery catheter. Furthermore, the elastomeric material could be filled with a radiopaque filler such as barium sulfate, particularly if it is only applied at the distal tip of the outer sheath. The overall length of the outer sheath is 54 cm from the delivery handle to the distal end of the outer sheath.

Delivery Handle

The handle is shown in cross section in FIG. 16. The inner catheter is attached to the delivery handle near the proximal end. The outer sheath is attached to the delivery handle at outer sheath mount mechanism 180, which is actuated by rotation of a rotating knob 176, near the proximal end. The outer sheath mounting mechanism 180 travels along a threaded rod inside a housing 192. The rotation of the rotating knob (relative to the housing and the inner catheter) rotates the threaded rod, which draws back the outer sheath. A pin 182 projects into the housing which stops the motion of the outer sheath after the aortic trunk graft is delivered. This pin prevents inadvertent deployment of the ipsilateral leg, until proper positioning is attained. The pin is removed following advancement and proper positioning of the ipsilateral leg component. Once the pin is removed, the outer sheath con continue to be retracted to expose the self-expanding ipsilateral leg graft.

Contralateral Leg Delivery System

Once the aortic trunk graft component and the ipsilateral leg graft component are delivered, the contralateral leg is delivered via the contralateral femoral artery. The contralateral leg graft component, as described above is preferably identical in construction to the ipsilateral leg component. However, since this is the only graft component being delivered on the contralateral side, the delivery catheter is somewhat different.

The contralateral delivery catheter is also comprised of an inner catheter, an outer sheath, and a delivery handle, and in many ways, the structure is quite similar. The inner catheter has a similar balloon tip construction, but it is smaller in diameter, since the delivery catheter only needs to contain the lower profile contralateral leg graft component.

The outer sheath is also smaller, preferably about 0.508 cm by 0.564 cm (0.200 in. by 0.222 in.). It is fabricated of a single layer of PTFE.

Since there is only one leg graft component, there is no proximal taper transition element for this delivery catheter, so the construction of the inner catheter is similar, with the exception of the region containing the proximal taper transition element. There is a leg stabilizing mechanism, similar to that on the ipsilateral delivery catheter which is positioned immediately proximal to the balloon. The stabilizing mechanism functions in the same manner as that for the ipsilateral delivery catheter.

Additional Embodiments

While the above graft system, with the trans-renal aortic attachment structure, is contemplated for use in a variety of anatomic conditions, particularly those with shorter necks, and those with tortuous aortas above the aneurysm, a somewhat different embodiment is contemplated for aneurysms with longer, and/or less tortuous aortic necks.

In this embodiment, the structure of the graft components and delivery catheter is identical with one exception. This "non trans-renal" design has no bare stent structure above the upper edge of the graft material. Barbs would be present (such as shown at 58 in FIG. 6A), but the aortic attachment stent would consist of only a single circular zigzag of struts, joined to the upper edge of the graft material via sutures, preferably by blanket stitching.

The advantage of this design for the graft system is that in relatively long necks, e.g., longer than 3 cm, there is little need for the extra securement provided by the above "trans-renal" structure, so utilizing a structure with no "trans-renal" structure presents no interference with the renal arteries.

Aortic Cuff

It is contemplated that in some instances, the aortic graft system embodiments described above may be inadvertently positioned too low in the aorta, leaving too little overlap with the "healthy" aorta of the upper neck of the aneurysm to form a robust seal. This erroneous placement has been observed with other endovascular grafting systems.

Figure 19:
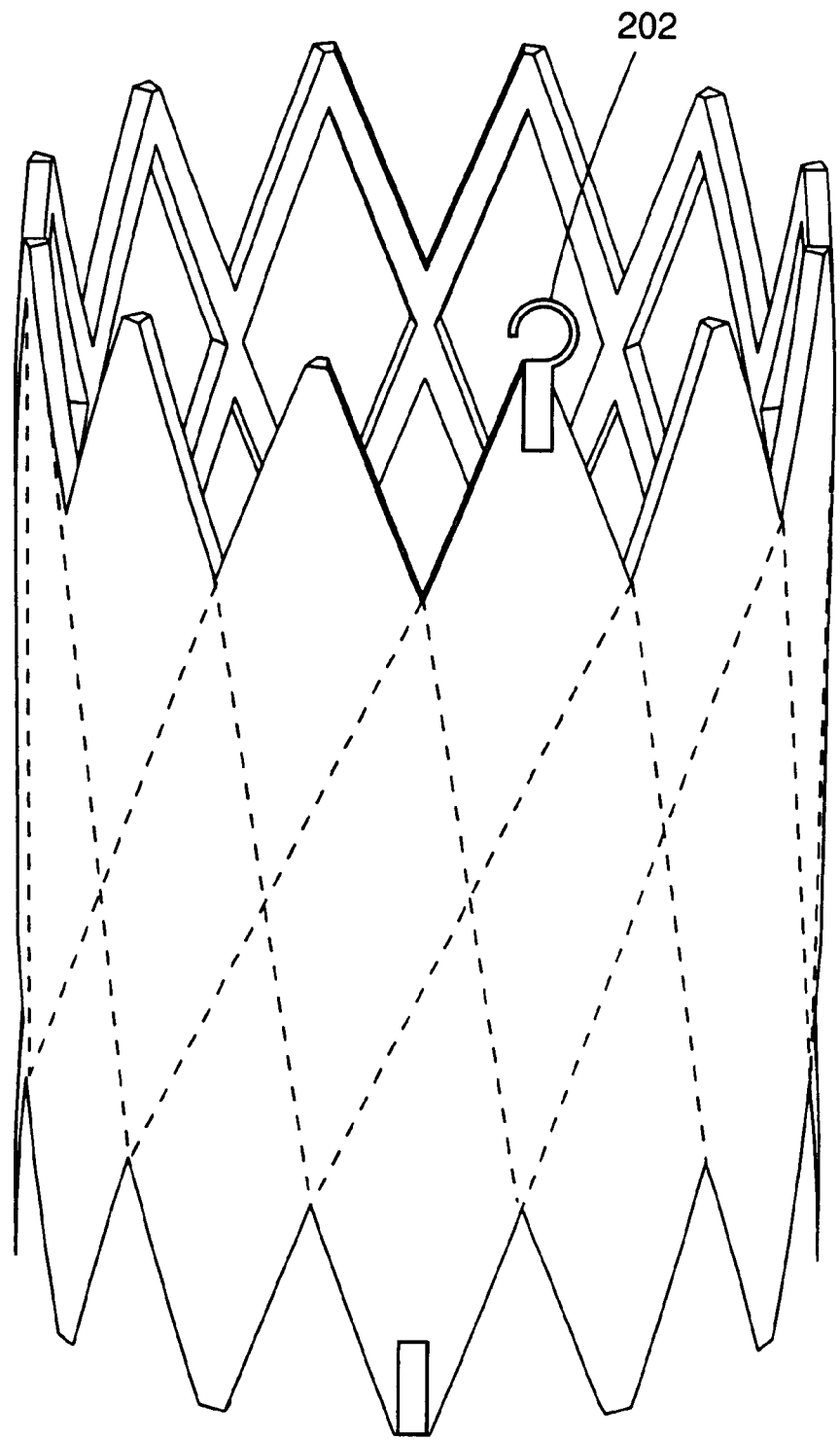
FIG. 19 is a perspective view of an alternative embodiment of the aortic stent of the present invention.

To help mitigate this problem, a short piece of graft material with an internal stent is contemplated. This is shown in FIG. 19. This "aortic" cuff is the same diameter as the already placed aortic trunk graft, but would be short, e.g. 2 to 4 cm in length. FIG. 19 is a perspective view of an aortic cuff. Inside is a self-expanding stent structure similar to the mid-stent, but with a cylindrical shape. The aortic cuff is implanted in an overlapping fashion inside the upper end of the aortic trunk, with a small length of aortic cuff projecting above the upper edge of the aortic trunk, to effectively result in a longer total overlap with the aortic neck. The aortic trunk is delivered via a delivery system similar to the contralateral leg delivery system. A similar inner catheter with a balloon tip, and outer sheath retractable via a delivery handle is utilized. Unlike the contralateral leg delivery system, however, the wire stabilization mechanism is positioned proximal to where the compressed and folded aortic cuff would reside in the delivery system. The eyelet 202 on the aortic cuff is on the caudal side, and engages with the wire stabilizing mechanism when loaded in the delivery catheter. By locating the stabilization mechanism on the caudal end of the aortic cuff, the aortic cuff is prevented from "jumping" out of the delivery catheter once the outer sheath is partially withdrawn, without stabilizing the caudal end, the relatively large diameter and relatively short length would cause the aortic cuff to "jump" cranially during delivery, resulting in mis-positioning.

It has been observed that any motion of stent structure against graft material can lead to graft wear, and subsequent holes. Since the aortic cuff structure would overlap on the inside of the aortic trunk, in an area with substantial motion set up by the aortic pulsatility, there is potential for relative motion to exist between these two structures. The "weak link" in this overlapped area is the graft material of the aortic cuff. The stent structure of the aortic trunk is able to have some small but significant relative motion, wearing a hole through the aortic cuff. After a hole is worn, the stents of the cuff and the trunk can rub against each other, causing subsequent failure of the struts.

To prevent such premature wearing of the graft material of this aortic cuff, it is contemplated to have two layers of graft material. In a preferred embodiment, two layers of the graft material described above would be sutured, preferably by blanket stitching, to the outside of the stent structure, in a manner similar to the attachment of the mid stent to the aortic trunk graft material. By utilizing two layers, the amount of time required to wear a hole through the graft material is significantly extended.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A delivery catheter for delivering an endovascular graft system at a desired location within a vessel of a patient's vascular system comprising:

a shaft;

a first graft component positioned about the shaft;

a second graft component positioned about the shaft, the first graft component being positioned distally of the second graft component, the first graft component being configured to be deployed in the vessel prior to deployment of the second graft component, the first and second graft components each having proximal and distal portions, the distal portion of the second graft component being configured to be deployed within the proximal portion of the first graft component;

a retractable sheath defining a lumen containing the shaft and first and second graft components, the sheath being configured to deploy the first graft component when the outer sheath is withdrawn a first distance and to deploy the second graft component when the outer sheath is withdrawn a second distance; and means for stabilizing the position of the distal portion of the second graft component with respect to the proximal portion of the first graft component when the sheath is being withdrawn the second distance.

2. The delivery catheter of claim 1 wherein the shaft has an outer surface and defines an inflation lumen and a guidewire lumen, the delivery catheter further comprising a balloon attached at a location spaced from a distal end of the catheter, the balloon having an interior in fluid communication with the inflation lumen.

3. The delivery catheter of claim 2 further having a transition element affixed to the balloon, the transition element having a distal portion between the balloon and the distal end of the catheter, the distal portion being configured to provide increasing stiffness from the distal end of the catheter to the balloon, the shaft, the balloon and the transition element together forming a portion of an inner catheter.

4. The delivery catheter of claim 3 wherein the distal portion of the transition element tapers outwardly from the distal end of the catheter to the balloon.

5. The delivery catheter of claim 1 wherein the retractable sheath has a distal end positioned about the balloon when in an unretracted position.

6. A delivery catheter for delivering an endovascular graft system at a desired location within a vessel of a patient's vascular system comprising:

a handle;

a shaft connected to the handle;

a first graft component positioned about the shaft;

a second graft component positioned about the shaft, the first graft component being positioned distally of the second graft component, the first graft component being configured to be deployed in the vessel prior to deployment of the second graft component, the first and second graft components each having proximal and distal portions, the distal portion of the second graft component being configured to be deployed within the proximal portion of the first graft component, the distal portion of the second graft component having a fastening element;

a retractable sheath defining a lumen containing the shaft and first and second graft components, the handle being configured to retract the sheath to deploy the first graft component when the outer sheath is retracted a first distance and to deploy the second graft component when the outer sheath is retracted a second distance; and a stabilizing element connected at one end to the handle and at another end to the fastening element of the second graft component, the handle stabilizing element and fastening element being configured such that the stabilizing element is retracted in a manner that disconnects the stabilizing element from the fastening element when the second graft component is deployed.

7. The delivery catheter of claim 6 wherein the distal portion of the second graft component includes a stent and wherein the fastening element is an eyelet fixed to the stent and the stabilizing element is a wire.

8. The delivery catheter of claim 7 further having a transition element affixed to the balloon, the transition element having a distal portion between the balloon and the distal end of the catheter, the distal portion being configured to provide increasing stiffness from the distal end of the catheter to the balloon, the shaft, the balloon and the transition element together forming a portion of an inner catheter.

9. The delivery catheter of claim 8 wherein the distal portion of the transition element tapers outwardly from the distal end of the catheter to the balloon.

10. The delivery catheter of claim 6 wherein the shaft has an outer surface and defines an inflation lumen and a guidewire lumen, the delivery catheter further comprising a balloon attached at a location spaced from a distal end of the catheter, the balloon having an interior in fluid communication with the inflation lumen.

11. The delivery catheter of claim 6 wherein the retractable sheath has a distal end positioned about the balloon when in an unretracted position.

* * * * *